United States Patent
Norling

(10) Patent No.: US 9,067,032 B2
(45) Date of Patent: *Jun. 30, 2015

(54) METHOD FOR TREATMENT OF LUNG INFECTIONS BY ADMINISTRATION OF AMINOGLYCOSIDES BY AEROLISATION

(71) Applicant: XELLIA PHARMACEUTICALS ApS, Copenhagen S (DK)

(72) Inventor: Thomas Norling, Lyngby (DK)

(73) Assignee: XELLIA PHARMACEUTICALS APS (DK)

( * ) Notice: Subject to any disclaimer, the term of this patent is extended or adjusted under 35 U.S.C. 154(b) by 8 days.

This patent is subject to a terminal disclaimer.

(21) Appl. No.: 14/041,023

(22) Filed: Sep. 30, 2013

(65) Prior Publication Data

US 2014/0041654 A1    Feb. 13, 2014

Related U.S. Application Data

(63) Continuation of application No. 13/178,930, filed on Jul. 8, 2011, now Pat. No. 8,598,131.

(60) Provisional application No. 61/363,330, filed on Jul. 12, 2010.

(30) Foreign Application Priority Data

Nov. 8, 2010 (NO) .................................. 20101576

(51) Int. Cl.
 *A61M 11/02*    (2006.01)
 *A61M 15/00*    (2006.01)
 *A61K 31/70*    (2006.01)
 *A61K 31/7036*    (2006.01)
 *A61K 9/00*    (2006.01)

(52) U.S. Cl.
 CPC .............. *A61M 11/02* (2013.01); *A61K 9/0078* (2013.01); *A61K 31/7036* (2013.01); *A61M 15/0065* (2013.01); *A61M 15/0091* (2013.01)

(58) Field of Classification Search
 None
 See application file for complete search history.

(56) References Cited

U.S. PATENT DOCUMENTS

| | | | |
|---|---|---|---|
| 5,508,269 | A | 4/1996 | Smith et al. |
| 6,987,094 | B2 | 1/2006 | Malvolti et al. |
| 2003/0149007 | A1 | 8/2003 | Chaudry et al. |
| 2004/0186064 | A1* | 9/2004 | Malvolti et al. ................. 514/36 |
| 2007/0071686 | A1 | 3/2007 | Lintz et al. |
| 2007/0116649 | A1 | 5/2007 | Charan et al. |
| 2012/0010162 | A1 | 1/2012 | Norling |

FOREIGN PATENT DOCUMENTS

| | | |
|---|---|---|
| EP | 2186508 A2 | 5/2010 |
| WO | 9513860 A1 | 5/1995 |
| WO | 02094217 A1 | 11/2002 |

OTHER PUBLICATIONS

Dopfer et al.; "Inhalation of Tobramycin in Patients with Cystic Fibrosis: Comparison of Two Methods"; Journal of Physiology and Pharmacology; 58(5); pp. 141-154; (2007).
Norwegian Search Report; Application No. 20101576; filed Nov. 8, 2010; 1 page.
Unterman, et al.; "Collagen Shield Drug Delivery: Therapeutic Concentrations of Tobramycinn in the Rabbit Cornea and Aqueous Humor"; J Cataract Refract Surg; 14; pp. 500-504; (1988).

* cited by examiner

Primary Examiner — Layla Bland
(74) Attorney, Agent, or Firm — Cantor Colburn LLP

(57) ABSTRACT

The present invention regards a novel administration form and a novel administration regime useful in the treatment and prevention of a bacterial lung infection in patient in need thereof, in particular by providing a composition useful for aerosolization of a highly concentrated solution of aminoglycosides such as Tobramycin.

18 Claims, 4 Drawing Sheets

METHOD FOR TREATMENT OF LUNG INFECTIONS BY ADMINISTRATION OF AMINOGLYCOSIDES BY AEROLISATION

CROSS-REFERENCE TO RELATED APPLICATIONS

This application is a continuation of U.S. application Ser. No. 13/178,930 filed on Jul. 8, 2011, which claims the benefit of Norwegian Application No. NO 20101576, filed Nov. 8, 2010, and U.S. Provisional Patent Application Ser. No. 61,363,330, filed Jul. 12, 2010, which are incorporated by reference herein in their entirety.

FIELD OF THE DISCLOSURE

This disclosure is related to the treatment of lung infections, especially in cases where the patient suffers from Cystic fibrosis.

BACKGROUND

Bacterial lung infection is a major problem and may become life threatening for patients suffering from chronic lung disorders, such as asthma, cystic fibrosis, and chronic obstructive pulmonary disease.

Specifically, cystic fibrosis (CF) is an autosomal recessive hereditary disease that affects approximately 30,000 people in the United States and approximately 40,000 in Europe. CF mutations occur in the gene encoding a chloride channel protein called the CF transmembrane conductance regulator (CFTR). Patients homozygous for defective CFTR genes typically suffer from chronic recurrent endobronchial infections (ultimately fatal) and sinusitis, as well as malabsorption due to pancreatic insufficiency, increased salt loss in sweat, obstructive hepatobiliary disease, and reduced fertility.

*Pseudomonas aeruginosa* (Pa) is the most significant pathogen in CF lung disease. Over 80% of CF patients eventually become colonized with Pa and the development of chronic infection of the lung with *Pseudomonas aeruginosa* is a typical feature of cystic fibrosis, which may induce further damage to the lung tissue and respiratory insufficiency, which is life threatening.

Tobramycin is an aminoglycoside antibiotic naturally produced by *Streptomyces tenebrarius*. It acts primarily by disrupting protein synthesis leading to altered cell membrane permeability, progressive disruption of the cell envelope and eventual cell death. Tobramycin is bactericidal at concentrations are equal to or slightly greater than its inhibitory concentrations.

To prevent and treat lung infections in patients with chronic lung disorders, antibiotics, such as aminoglycoside antibiotics, are widely used. Parenteral aminoglycosides are highly polar agents and penetrate poorly into the endobronchial space. Furthermore, aminoglycoside binding to sputum (International Cystic Fibrosis [Mucoviscidosis] Association, 1995 Annual Questionnaire, Paris, France; 1995, Collins F S., "Cystic fibrosis molecular biology and therapeutic implications", Science 1992; 256, pp 774-779, Davis P B, et al., "Cystic fibrosis", Amer J. Respir Crit Care Med 1996; 154(5), pp. 1229-56 or to sputum glycoproteins or DNA (Koch C, Hoiby N., "Pathogenesis of cystic fibrosis", Lancet 1993; 341(8852, pp. 1065-1069) reduces bioactivity and requires local concentrations 10- to 25-fold above the minimal inhibitory concentration (MIC) to overcome reduced aminoglycoside availability to bacterial targets. To obtain adequate drug concentrations at the site of infection with parenteral administration, serum levels approach the levels associated with severe side effects such as nephrotoxicity, vestibulotoxicity, and ototoxicity (Konstan M W, Berger M. Infection and inflammation of the lung in cystic fibrosis. New York, N.Y. Dekker; 1993, FitzSimmons S C, The changing epidemiology of cystic fibrosis. J Pediatr 1993; 122:1-9).

Aerosolized administration of aminoglycosides offers an attractive alternative to parenteral administration, delivering high concentrations of antibiotic directly to the site of infection in the endobronchial space, while minimizing systemic bioavailability.

Aminoglycosides such as Tobramycin are often aerosolized using a nebulizer, i.e., an energy powered device that converts a liquid aminoglycoside formulation into a mist, which is then administered to the patient by breathing the formed mist into the lungs through a face mask or mount piece. A commonly used nebulizer for administration of aerosol formulations is the Jet nebulizer, also called "atomizers". Jet nebulizers are connected by tubing to a compressor that causes compressed air or oxygen to blast at high velocity through a liquid medicine to turn it into an aerosol to be inhaled by the patient.

Jet nebulizers are also used for the administration of a commercially available formulation of Tobramycin solution for inhalation (TOBI®; 60 mg/mL in 5 mL of ¼ normal saline), developed by PathoGenesis Corporation (now Novartis). TOBI® was approved by the US Food and Drug Administration in 1997 for twice-daily use in CF patients over 6 years of age.

Various formulations of Tobramycin solutions for inhalation are also described in the prior art. For example, U.S. Pat. No. 5,508,269 discloses a formulation comprising from 40-100 mg of aminoglycoside in 1 ml of saline diluted into a quarter normal saline strength, wherein the formulation has a pH between 5.5 and 6.5, and wherein the solution is delivered in a 5 ml concentrated form by aerosolization.

U.S. Pat. No. 6,987,094 discloses an aerosol formulation consisting of 75 mg/ml of Tobramycin dissolved in an aqueous solution containing 0.45% w/v sodium chloride, wherein the pH is between 4.0 and 5.5, and the osmolarity ranges between 250 and 450 mOsm/l.

US patent publication 2007/0116649 suggests aerosol formulations comprising from about 100 mg/ml to 200 mg/ml of anti-gram-negative antibiotics. Tobramycin formulations are suggested, but no experiments with Tobramycin are disclosed.

US patent publication 2007/0071686 discloses a Tobramycin composition comprising about 80-120 mg/ml Tobramycin, an acidic adjuvant, and only a low concentration of sodium chloride. The acidic adjuvant may be sodium sulphate or sodium phosphate. According to US 2007/0071686, the concentration of the active agent should not exceed 120 mg/ml as higher concentrations of Tobramycin are said to have a negative effect on nebulization due to the viscosity of the composition. Furthermore, the Tobramycin composition according to US 2007/0071686 is to be administered to the patient by the use of a nebulizer, i.e., the active ingredient is inhaled by tidal breathing.

EP 2186508 describes, inter alia, a composition of less than 4 ml of a solution comprising 60-200 mg/ml aminoglycoside antibiotic in a physiologically acceptable carrier. The experiments reported in EP 2186508 show that the time necessary for administering a composition comprising 120 mg/ml Tobramycin using PART LC PLUS™ jet nebulizer (Pari Boy N compressor, Starnberg, Germany) is about 10 min. Although this might be less than the time required for administering commercial available TOBI®, the time required it still too long from a patient compliance and patient user-friendly point of view. Using a breath actuated inhalation device, EP 2186508 reports of faster administration time than that achieved with the mentioned commercially available system. However, the administration time achieved with the breath actuated inhalation device used (AcroDose™) in the experiments reported in EP 2186508 is obtained using a composition having a low Tobramycin concentration (only 60 mg/ml). It is furthermore reported that with the administration of a 60 mg/ml composition using the AcroDose™ system, a second aliquot may have to be administered as well. The need for filling and administration of a second aliquot represent a disadvantage from a patient friendly and compliance point of view.

Tobramycin solutions are also known for topical administration, e.g., in the treatment of keratitis; cf. Davis et al. (1978), Canad. J Ophtal., 13:273, 1978, Davis et al., 1978, Arch Opthalmol, vol 96, page 123-125, and Unterman et al. (1988), J. Cataract Refract. Surg., vol. 14, page 500-504.

A well-known drawback with the available administration means and treatment regimes is the time required for administration, affecting inter alia patient compliance and the patient's quality of life.

Dopfer et al., "Inhalation of Tobramycin in patients with cystic fibrosis: Comparison of two methods", Journal of Physiology and Pharmacology, 2007, 58, suppl. 5, pp. 141-154, reports the results of a monocentric, open label, crossover study wherein various amounts of Tobramycin (TOBI®) was administered using different inhalations systems, i.e., the well known PARI-LC PLUS® nebulizer (Pari Boy N compressor, Starnberg, Germany) and AKITA® combined with PARI LC PLUS® nebulizer (Activaero, Gemüden, Germany). The study showed that by using the AKITA® system, the time required for aerosol inhalation was reduced from about 20 minutes to about 7-8 minutes. The study further showed that similar serum concentrations were obtained by the two methods of said clinical study.

Although the use of the AKITA® administration device reduces the time needed for administration of an effective dose of Tobramycin compared with the common administration system, the time needed is still too long. There is therefore still a need for a treatment regime ensuring shorter administration times resulting in better compliance and quality of life for cystic fibrosis patients and patients having other lung disorders being treatable with Tobramycin.

In addition, the prior art systems and methods for administering aminoglycosides to the lung of a patient by inhalation suffer from further drawbacks such as that the amount of active ingredients not reaching the site of action due to the fact that remnants of the formulations remain in the nebulizer device after administration of the Tobramycin formulation or disappear out in the surroundings of the patients. From an economical and environmental point of view, there is thus also a need for administration regimes wherein lower amounts of the Tobramycin formulation are wasted.

It is therefore an object of the present disclosure to provide an improved administration regime for aminoglycosides which are not encumbered with the drawbacks of the prior art.

SUMMARY

The present disclosure provides a novel administration form and a novel regime for the treatment and prevention of lung infections with aminoglycoside antibiotics, in particular Tobramycin. The present disclosure provides for a fast and efficient administration of aminoglycoside antibiotics compared with the prior art. Compared to the administration regime available on the market (TOBI® administered using the PARI LC® nebulizer), the administration regime according to the present disclosure provides an effective dosage of Tobramycin in just a few minutes, e.g. 1-5 minutes.

The present inventors have surprisingly found that the highly concentrated solution of Tobramycin in combination with the small volume of administered formulation provides for an efficient and improved dosing regime.

In addition, the administration form and the administration regime according to the present disclosure provides twice as much of the active ingredient, such as e.g., Tobramycin formulation, to be administered to the lungs compared to the prior art administration regimes. A further advantage of the present administration regime is that the void volume, and hence waste remaining in the inhalation device, used according to the present disclosure is negligible compared to the prior art administration regimes. By waste is also understood the fine particles which are exhaled into the air when using the Pari nebulizer. Active drug, and antibiotics in particular, should stay at the site of action and not be present in general surroundings. For example, low concentrations of antibiotics might induce resistant microorganisms.

Yet another advantage of the present disclosure is that the mean maximal plasma concentration obtained according to the present disclosure are lower compared with the mean maximal plasma level obtained using prior art administration regimes (Tobramycin using TOBI® and PARI LC® nebulizer).

According to one aspect of the disclosure, a composition for therapeutic or prophylactic treatment of bacterial infections in the pulmonary system of a patient in need thereof is provided, wherein the composition comprises 150-250 mg/ml Tobramycin, wherein the composition is to be administered by inhalation.

According to another aspect of the disclosure, a composition for therapeutic or prophylactic treatment of bacterial infections in the pulmonary system of a patient in need thereof is provided, wherein the composition comprises 150-250 mg/ml aminoglycoside for therapeutic or prophylactic treatment of bacterial infections in the pulmonary system of a patient in need thereof, wherein the composition is to be administered by inhalation and wherein the composition is substantially free of sodium chloride.

Yet another aspect of the present disclosure includes a composition which is to be administered by inhalation of monodisperse droplets formed by aerosolization of the composition, the droplets having a mass median aerodynamic diameter of 4-7 μm.

A further aspect of the present disclosure includes a composition for therapeutic or prophylactic treatment of bacterial infections in the pulmonary system of a patient in need thereof comprising 150-250 mg/ml aminoglycoside, wherein the composition is to be administered by inhalation of aerosols in the form of monodisperse droplets having a mass median aerodynamic diameter of 4-7 μm.

According to one embodiment of the present disclosure, the aminoglycoside is Tobramycin.

According to yet another embodiment of the present disclosure, the composition comprises Tobramycin sulphate corresponding to 150-250 mg/ml Tobramycin, e.g. such as corresponding to 180 mg/ml Tobramycin. Such a composition may, according to one embodiment, be administered by inhalation, wherein the inhalation is to be performed in less than four minutes, preferably less than three minutes, more preferably less than two minutes, more preferably less than one minute.

According to another embodiment of the present disclosure, the composition comprises Tobramycin sulphate dissolved in water, wherein the pH is optionally adjusted so that the pH is 6-8.

According to yet another embodiment of the present disclosure, the composition is to be administered by inhalation, wherein said inhalation is to be performed in 1-5 minutes.

According to a further embodiment, the inhalation is to be performed in less than four minutes, preferably less than three minutes, preferably less than two minutes, more preferably less than one minute.

According to another embodiment of the present disclosure, the composition has a volume of up to 500 µl.

According to a further embodiment of the present disclosure, the present composition provides for the administration of a total amount of aminoglycoside to a patient in need thereof of 50-80 mg.

According to yet another embodiment of the present disclosure, the present composition provides for the administration of a unit dosage comprising 60-70 mg Tobramycin, wherein the administration is to be performed in less than 5 minutes.

According to yet another embodiment of the present disclosure, inhalation of the composition provides for the administration of 63 mg Tobramycin (180 mg/mL×0.35 mL) to the pulmonary system of the patient in need thereof, wherein the composition is to be inhaled by the patient performing 7 deep, slow inhalations.

According to yet another embodiment, the present composition has an osmolality of between 300 and 500 mOsmol/kg, preferably 375 and 475 mOsmol/kg.

According to a further embodiment of the present disclosure, the composition is useful for administration using a metered dose inhaler having a spray nozzle unit providing the formation of said aerosols by transferring the composition through orifices having a diameter of 1.8-3.9 µm.

The composition according to the present disclosure may be administered using a metered dose inhaler that provides a working pressure of 20-80 bar, such as e.g. 30-40 bar, preferably 35 bar.

The composition according to present disclosure may furthermore be administered with a flow of 10-50 L/min.

The composition according to the present disclosure may be administered using metered dose inhalers suitable for breath actuated inhalation or by coordinated inhalation.

The composition of the present disclosure is furthermore specifically useful in the treatment of infections in the pulmonary system caused bacteria of the genus *Pseudomonas*.

The composition of the present disclosure is furthermore specifically useful in the treatment of infections in the pulmonary system, wherein the patient suffers a chronic lung disease such as cystic fibrosis.

DETAILED DESCRIPTION

Definitions

Figure 1:
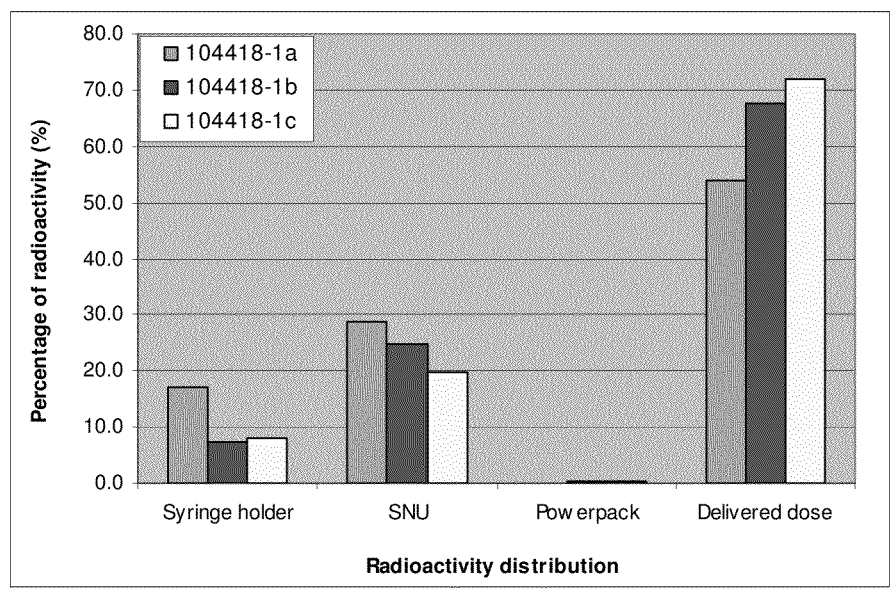
FIG. 1 shows the mass balance of radiolabelled 20% w/v Tobramycin solution delivered in vitro using a Tobrair® device (6 actuations).

The term "aminoglycosides" as used herein is meant to embrace antibiotic compounds comprising aminosugars, the compounds being naturally produced by *Streptomyces* or *Micromonospora*, but also synthetic and semisynthetic derivatives thereof "Aminoglycosides" is thus meant to include antibacterial compounds such as, e.g., tobramycin, streptomycin, apramycin, paromomycin, thodostreptomycin, neomycin, kanamycin, amikacin, arbekacin, capreomycin, and netilmicin, Tobramycin, (2S,3R,4S,5S,6R)-4-amino-2-{[(1S,2S,3R,4S,6R)-4,6-diamino-3-{[2R,3R,5S,6R)-3-amino-6-(aminomethyl)-5-hydroxyoxan-2-yl]oxy}-2-(hydroxymethylcyclohexyl]oxy)-6-(hydroxymethyl)oxane-3,5-diol, registry no 32986-56-4 assigned by Chemical Abstracts Service (CAS) can be presented by the following formula:

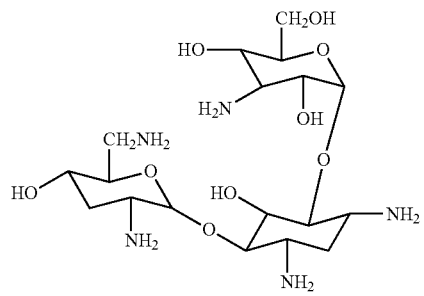

"Tobramycin sulphate" is a salt with the Registry no 49842-07-1 assigned by Chemical Abstracts Service (CAS). The salt in solid form comprises Tobramycin and sulfate in the ratio 2:5.

The term "aqueous Tobramycin sulphate" is meant to embrace aqueous solutions comprising Tobramycin and sulphate-ions in any ratio.

A "highly concentrated solution of aminoglycoside" is any solution comprising more than 100 mg aminoglycoside per ml, such as e.g., a solution comprising 180 mg gentamycin per ml. For Tobramycin, a highly concentrated solution is herein meant a Tobramycin solution comprising 150-250 mg/ml Tobramycin, optionally in form of Tobramycin sulphate.

A pharmaceutical formulation comprising Tobramycin could be obtained by dissolving Tobramycin or Tobramycin sulphate in sterile water. The pH of such formulations may be adjusted to levels suitable for pulmonary delivery.

A suitable pH of the composition according to the present disclosure may be 6-8. The pH of the aminoglycoside formulation, e.g., in case where the aminoglycoside is Tobramycin, may be adjusted by the addition of sulphuric acid.

A suitable composition of the present disclosure consists of Tobramycin sulphate and water, wherein the amount of Tobramycin sulphate corresponds to 180 mg/ml Tobramycin, and wherein the pH of said composition is 6-8.

According to one aspect of the disclosure, the present composition is substantially free of sodium chloride. The term "substantially free of sodium chloride" means that no sodium chloride is added to the solution of tobramycin (e.g. tobramycin dissolved in sterile water). Thus, the only sodium chloride present in a composition that is substantially free of sodium chloride is due to sodium chloride present being contained in the water used to dissolve the Tobramycin, such as Tobramycin sulphate.

The term "therapeutic dose" as used herein is to be understood to be the dose that when administered to the patient in accordance with the present disclosure results in decreased levels of *Pseudomonas* bacteria in the lungs or results in reduced growth rate of *Pseudomonas* bacteria in the lungs.

The mean maximal plasma concentration is obtained by administering a formulation comprising at least 100 mg/ml aminoglycoside, such as e.g., 150-200 mg/ml aminoglycoside, such as e.g. 180 mg/ml aminoglycoside according to the present disclosure. The mean maximal plasma concentration according to this disclosure is lower than obtained by the treatment regime of TOBI® with the Pari LC® Plus nebulizer.

According to the present disclosure, a composition comprising a highly concentrated solution of an aminoglycoside, such as e.g., 150-250 mg/ml Tobramycin, is used in the treatment and prevention of lung infections wherein said composition is suitable for the aerosolization providing monodisperse droplets having a mass median aerodynamic diameter (MMAD) of 4-7 µm. "MMAD" is thus to be understood as the mass median aerodynamic diameter of the droplets/aerosols.

An aqueous Metered-Dose Inhaler (aMDI) is a device that delivers a specific amount of medication to the lungs, in the form of a short burst of droplets of medicine that is inhaled by the patient.

A nebulizer is a device used to administer liquid medication in the form of a mist which is continuously inhaled into the lungs by tidal breathing. Typical administration time is 20 minutes of continuous and steady breathing through a mask. A well known device used to administer Tobramycin according to the prior art administration regimes is the PARI LC® PLUS device system. When administering a pharmaceutical agent using a nebulizer, the patients inhale the aerosols formed by the device by tidal breathing. This is in contrast to the metered dose inhalers suitable according to the present disclosure, where the inhalation is coordinated with actuation of the inhaler. Thus the administration comprises one inhalation for each actuation of the device. The actuation of the device can be triggered by various means known in the field, e.g. manually or by "breath sensors".

When a metered dose inhaler is actuated by the use of breath sensors and thus by inhalation only, the composition is administered by "breath actuated inhalation". When a metered dose inhaler is actuated manually at the same time as the patients performs one inhalation, the composition is administered by "coordinated inhalation".

Typical administration time for one inhalation with an aMDI is a few seconds. This maneuver can be repeated several times to obtain the desired dose.

The most preferred aMDIs for use in the present disclosure produce monodisperse particles with a mass median aerodynamic diameter (MMAD) of approximately 5-5.7 µm (GSD<1.6).

It is well known that pulmonary penetration is predominantly dependent on particle size and inhalation flow rate. Since pulmonary penetration increases with decreasing particle size (MMAD) over the range 1-5 µm, and with larger particles generally impacting in the oropharynx and large airways and particles less than 1 µm generally being exhaled. According to one aspect of the present disclosure, the composition is to be administered by inhalation of monodisperse droplets formed by aerosolization of said composition, said droplets having a mass median aerodynamic diameter of 4-7 µm using a suitable metered dose inhaler providing a flow of 10-50 L/min. The metered dose inhaler may comprise a constrictor to regulate the flow rate.

Several metered dose inhalers are known to the skilled person. A metered dose inhaler is usually designed for administration and delivery of a specific dose of a pharmaceutical formulation to the lungs which upon operation by the patient, provides a short burst of aerosolized formulation, which is thus inhaled by the patient. In summary, a metered dose inhaler usually comprises the following components:

i) a container comprising the formulation for aerosolization having a proximal opening allowing the composition to be expelled therefrom, ii) a metering device providing the delivery of a predetermined amount of the formulation to be delivered when operating the device, such as e.g., by providing force to be applied on an axially movable piston;

iii) a power pack consisting of a means enabling the metering and delivery of the composition; and iv) a mouthpiece including a spray nozzle unit (SNU) providing the formation of aerosols and through which the aerosolized medicament is inhaled by the patient operating the device, thus resulting in the delivery of the aerosols of the composition into the lungs of the patients.

Means for enabling the metering and delivery of the composition may, e.g., be provided with a dose knob which is available on the outside of the metered dose inhaler device providing the transfer and delivery of a predetermined amount of the medicament to be administered to the patient, and wherein accumulating force transferred from the dose knob to the piston creates a pressure inside the medicament container. Such a pressure may also be achieved by any power source well known to the skilled person, such as e.g., electrical force (battery), mechanical force (muscle), or physical force (propellant).

Any metered dose inhaler providing aerosols of a highly concentrated aminoglycoside formulation having a mass median aerodynamic diameter of 4-7 µm may be used to according to the present disclosure. Thus, a suitable metered dose inhaler useful for administering the composition of the present disclosure may be a metered dose inhaler suitable for coordinated inhalation of the composition or suitable for breath actuated inhalation, as long as the metered dose inhaler comprises a SNU forming aerosols of a highly concentrated aminoglycoside formulation having a mass median aerodynamic diameter of 4-7 µm and wherein said metered dose inhaler comprises a means for providing the desired pressure ensuring the transfer of the composition of the present disclosure from the container through the SNU upon inhalation and actuation of the inhalator.

According to the present disclosure, "droplets" or "aerosols" are aerosolized liquid particles comprising a pharmaceutical formulation, such as a highly concentrated solution of aminoglycoside.

"GSD" is the geometric standard deviation.

The "Tobrair® device" as used in herein and as referred to in the examples below, is an aqueous metered dose inhaler (MDI) which produces monodisperse droplets of a composition comprising high concentrations of Tobramycin having a MMAD of 4-7 µm.

A suitable metered dose inhaler useful for administration of a formulation comprising a highly concentrated solution of an aminoglycoside, such as a solution of 150-250 mg/ml Tobramycin, e.g., in the form of Tobramycin sulphate, is described in WO 2011/043712, which is incorporated herein by reference.

The spray nozzle unit (SNU) is placed in the mouthpiece of the metered dose inhaler used according to the present disclosure enabling the creation of the near mono-disperse droplets upon inhalations (breath actuated or coordinated inhalation) and operation of the device by the patients. More particular, when e.g. applying force on a dose knob, thus triggering the actuation of the power pack, and by coordinated breathing placing the mouth piece in the mouth of the patient operating the device, the composition is transferred from the container to the mouth piece and forced through the SNU, resulting in the formation of aerosols having a mass median aerodynamic diameter of 4-7 µm which is to be inhaled. The SNU comprises a plurality of through passing orifices providing the formation of said aerosols.

A suitable spray nozzle unit (SNU) to be used in a metered dose inhaler for the provision of aerosols having a mass median aerodynamic diameter of 4-7 µm and comprising a high concentrated solution of an aminoglycoside is described in WO 02/18058, which is incorporated herein by reference.

Figure 6:
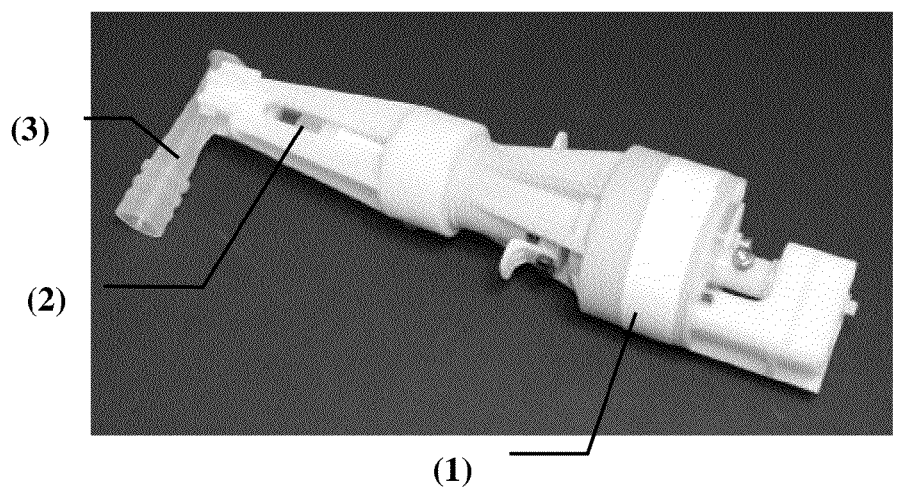
FIG. 6 shows a suitable inhalator comprising a reusable power pack (1), a disposable drug container (standard syringe) (2) and a mouthpiece with a spray nozzle unit (3).

In FIG. 6, an aqueous metered dose inhaler is shown that may be used in accordance with the present administration regime. The device comprises a reusable powerpack (3), a syringe holder, a disposable drug container (standard syringe (2)) and a mouthpiece including a spray nozzle unit (SNU) (1).

An aMDI suitable for the administration of a composition according to the present disclosure is capable of forming distinct and uniform aerosol droplets of a mean diameter of 4 to 7 microns of a high viscosity liquid. WO 95/13860 describes membrane filters provided with pores having a pore size of typically between 5 nm and 50 µm. Membranes disclosed therein having pores of a size providing aerosols having a mass median aerodynamic diameter of 4-7 µm may preferably be used in a spray nozzle unit placed in a metered dose inhaler, such as e.g., a metered dose inhaler disclosed in WO 2011/043712, to administer a highly concentrated Tobramycin composition according to the present disclosure.

According to a preferred embodiment of the disclosure, the aerosols formed by the metered dose inhaler is provided using a spray nozzle unit as described in Respiratory Drug Delivery 8, 2002, by Wissink and van Rijn, which is incorporated herein by reference. The use of smart micro nozzles disclosed therein provides perfect Rayleigh break-up with orifices <10 µm at trans-nozzle pressures under 5 bar, with jet characteristics shifting from viscous to kinetic. For the present disclosure, when the composition comprises 150-250 mg/ml aminoglycoside, the metered dose inhaler preferably provides a working pressure of 20-80 bar, more preferably 30-40 bar.

According to the present disclosure, the SNU includes a means for the formation of aerosols of the formulation of a highly concentrated solution of an aminoglycoside having a mass median aerodynamic diameter of 4-7 µm (c.f. Wissink and van Rijn (2008), supra). According to one embodiment, the SNU is composed a silicon chip (the mesh) (4) and plastic moulded parts of medical grade plastic (cf. FIG. 7).

Figure 8:
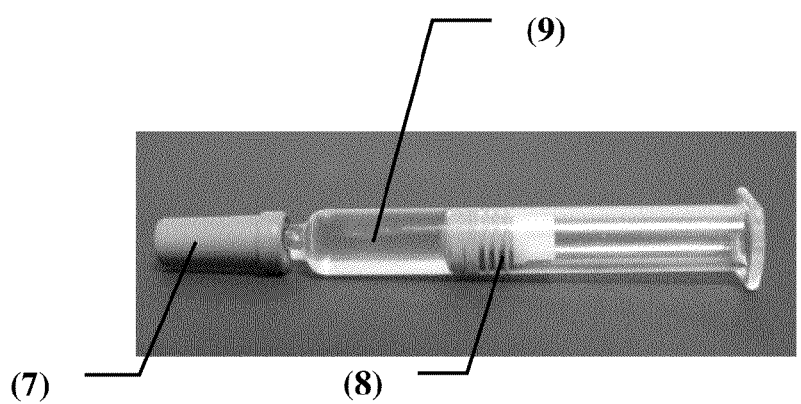
FIG. 8 shows a syringe which may be inserted into the device, having a protective cap (7) that may be removed and a piston (8) for the transferring of the content of the syringe (9) into the device.

The container comprising the formulation for aerosolization to be inhaled may according to one embodiment be a syringe (10), such as a 1 ml syringe. A suitable 1 ml syringe having a movable piston (8) and a removable and protective cap (7) which is removed prior to the insertion of the syringe in the metered dose inhaler is shown in FIG. 8.

A metered dose inhaler suitable for the present administration regime may comprise a dose knob. When the patient applies pressure on the dose knob on the metered dose inhaler, the device is actuated and the piston (8) will move a predetermined distance providing the transfer of the appropriate dose from the syringe through the SNU.

When the device is actuated, then the piston (8) will move a certain distance (equivalent to approx. 50 µl) and the liquid will be pressed through the holes in the silicon chip (the mesh), thereby creating the droplets which are subsequently inhaled. This can be repeated the required number of times to deliver a total inhaled dose.

Figure 7:
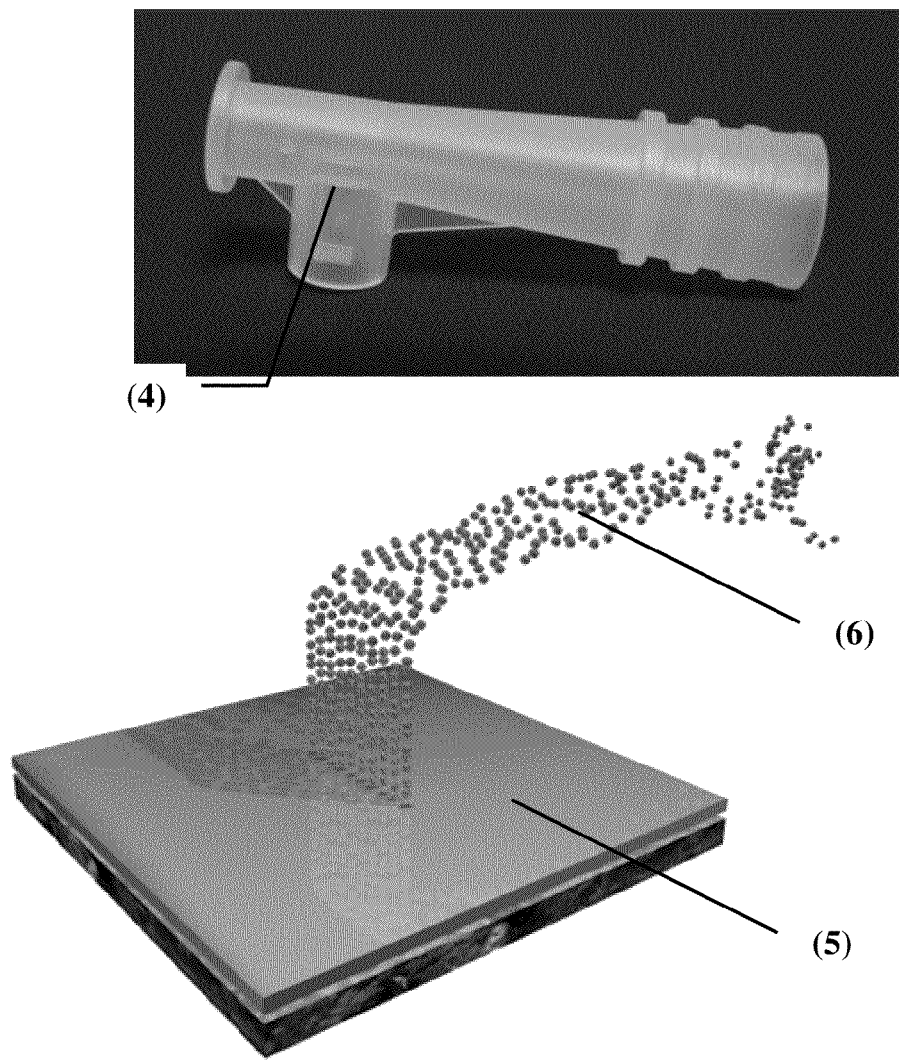
FIG. 7 shows a mouthpiece with a spray nozzle unit (4), having a silicon chip (5) providing droplets (6) by Rayleigh breakup.

For example, the piston may when moved result in that predetermined amount of the formulation comprising a highly concentrated solution of aminoglycosides to be transferred and pressed through the orifices of the SNU providing the formation of aerosols having a mass median aerodynamic diameter of 4-7 µm. The aerosols are thus formed when pressing the formulation comprising a highly concentrated solution of aminoglycosides through the holes (orifices) in SNU, such as the silicon chip (the mesh) (5), thereby creating the droplets which are subsequently inhaled (FIG. 7). This can be repeated the required number of times to deliver a prescribed dose.

The skilled person will understand that to be able to transfer a viscous solution through a set of uniformed sized holes placed in e.g., a silicon plate or membrane in a SNU for the formation of a set of small aerosols according to the present disclosure an appropriate pressure will have to be applied. A metered dose inhaler used according to the present disclosure is able to provide a working pressure of 20-80 bar. Preferably, when a composition comprising 180 mg/ml Tobramycin sulphate is to be inhaled, the dose metered inhaler used according to the present disclosure is able to provide a working pressure of 30-40 bar, preferably 35 bar.

The composition according to the present disclosure will when pressed through the SNU of the aMDI leave the holes as distinct droplets with a diameter approx. 1.8 times the diameter of the holes. Thus, a suitable diameter of the orifices present in the SNU through which the composition is to be transferred according to the present disclosure may be 1.8-3.9 µm. The droplets are then channeled to the lungs upon actuated breathing through a mouthpiece that avoids extensive droplet coalescence.

The suitable inhalators referred to above comprising suitable nozzles will furthermore be able to form aerosols of a composition having a viscosity up to 5 mPaS at high shear rates <50 l/S.

The suitable inhalators will provide a flow of 10-50 L/min.

The present disclosure has several advantages over the prior art. The administration time is less than 5 minutes compared with 20-30 minutes using the prevailing administration system available (TOBI®/PARI LC® PLUS nebulizer). Furthermore, by administering a lower amount of Tobramycin in total, the present disclosure still provides the delivery of higher amounts of Tobramycin to the lungs (see table 12 and table 13). In addition, the method of the present disclosure results in lower plasma levels of Tobramycin compared with said prevailing administration system (see table 19). It is surprising that the administration of quite a lower amount of active ingredient still results in higher amount of the active ingredients in the lung. It is furthermore surprising that the method of the present disclosure, even though it provides higher amounts of the active ingredients in the lungs, still results in lower plasma concentration of the active ingredient compared with the plasma levels obtained applying the prevailing administration regime. (see table 19) The lower plasma concentration obtained by the present method is further an improvement over prior art as plasma concentrations of Tobramycin is involved with undesired side effects.

According to one aspect of the present disclosure, a pharmaceutical solution comprising 180 mg Tobramycin per ml water is used. This corresponds to approximately 3 fold the concentration of the solution in the marketed product (TOBI®). Tobramycin at 60 mg/mL is known to be well tolerated in healthy volunteers even at higher total dose levels; however it is considered that this increase in concentration potentially increases the risk of local irritation, but is not considered to be the primary driver for systemic exposure or systemic side effects in this study since the total dose level is lower. The result of the clinical study performed in connection with the present disclosure revealed that there were only a few incidents of local irritation when subjected to the treatment regime of the present disclosure.

EXAMPLES

The invention will now be described in light of the following experimental data. It is to be understood that the examples are not to be interpreted as limiting for the scope of the present invention.

Materials

In the following examples, in vitro experiments and in vivo clinical studies are presented wherein the prevailing Tobramycin inhalation solution (TOBI®) delivered using the prevailing nebulizer (PARI LC® PLUS jet nebulizer) have been compared with a Tobramycin inhalation solution delivered using a Tobrair® device, providing aerosols having the mass median aerodynamic diameter in the range of 4-7 µm according to the present disclosure.

The said tested Tobramycin solutions have the following characteristics:

| Product | Concentration | Delivered volume | Delivered dose | pH |
|---|---|---|---|---|
| Tobramycin solution according to the present invention | 180 mg/mL | 350 µL | Approximately 60 mg | 7-8 |
| Tobi ® | 60 mg/mL | 5000 µL | 300 mg | 5.3-6.3 |

The standard treatment with 300 mg of Tobramycin using 5 mL in a Pari nebulizer will only result in approx. 10% of the dose reaching the lungs. For the Tobrair® device this is between 20 and 60% of the labelled dose.

The droplets produced by a suitable aMDI, such as the Tobrair® device, have a mass median aerodynamic diameter in the range of 4-7 µm.

The Tobramycin solutions used in the following examples was prepared by dissolving 81.5 g Tobramycin sulphate in 300 ml water. The solution administered to the patient in the in vivo study thus corresponds to the administration of about 63 mg Tobramycin (0.35 ml of 180 mg/ml Tobramycin).

Example 1

In Vitro Delivery of Tobramycin

Prior to a clinical study, an in vitro experiment was conducted to demonstrate that a solution of Tobramycin according to the present disclosure can be radiolabelled and the level of the radioactivity to be delivered is safe to the volunteers and sufficient for the scintigraphic imaging. Furthermore, the experiments also provided information about amount of Tobramycin solution left in the various parts of the nebulizer system used.

The following solutions were used in the in vitro experiment:

18% w/v w/v Tobramycin solution, Xellia, BN:80000991 and 80000992

20% w/v w/v Tobramycin solution, Xellia, BN:80000981

TOBI® 300 mg/5 mL Tobramycin solution, Novartis, BN:X003812

Sodium pertechnetate solution (eluted from $^{99m}$Tc-Generator), IBA, BN: A-AJY-05 and A-ALL-13

$^{99m}$Tc-DTPA kit, Coviden, BN: 292786, 290187 and 294814

Radiolabelling of the 20% w/v Tobramycin solution

Based on the clinical protocol (example 2), the Tobrair® device was intended to deliver 60 mg Tobramycin to the volunteers, i.e., 20% w/v solution×0.3 mL over 6 inhalations. Therefore, the 20% w/v Tobramycin solution was radiolabelled for testing using the Tobrair® device. The $^{99m}$Tc (sodium pertechnetate) solution was eluted from the Technetium Generator and the required volume added into a DTPA kit and mixed thoroughly. The radioactivity of the resulting $^{99m}$Tc-DTPA solution was measured and the vial was sealed and stored in a lead pot before use. 15 mL of 20% w/v Tobramycin solution was filtered through a 0.20 µm filter and transferred into a clean scintillation vial. Approximately 0.15 mL of $^{99m}$Tc-DTPA solution containing 642 MBq radioactivity was then added into the drug solution and thoroughly mixed with magnetic stirring. No change in colour of the Tobramycin solution or drug precipitation was observed after the radiolabelling indicating compatibility of the radiolabel with the drug product. The radioactivity level in the resulting Tobramycin solution was 42.8 MBq/mL giving 12.8 MBq radioactivity per 0.3 mL dose. The total volume of the $^{99m}$Tc-DTPA solution in the final drug solution was approximately 1.0% which will not have any significant impact on the properties of the final drug solution (e.g. viscosity) and hence will not affect device performance.

In Vitro Delivery of the 20% w/v Tobramycin Using Tobrair® Device

In vitro Tobramycin delivery via the Tobrair® device was characterized using a Copley flow pump, Model no: HCP2, at a continuous flow rate of 45 L/min (n=3).

Prior to the test, approximately 0.5 mL (0.3 mL plus sufficient overage) of the radiolabelled 20% w/v Tobramycin solution was loaded into the drug cartridge (1 mL glass syringe) following the instruction provided by Medspray (Instructions for Use of Tobrair test device, SHL GROUP, 11 Jan. 2010, 2 Mar. 2010 and 6 Apr. 2010) and the radioactivity measured. The drug cartridge (syringe) was then assembled into the Tobrair® device. After priming, the residual formulation in the spray nozzle unit (SNU) was removed using a piece of tissue. The total weight of the device (together with the drug cartridge) was measured before connecting it to the inhalation filter (for dose collection) and then the Copley flow pump. After 6 actuations, the weight of the device was measured again to calculate the weight loss (delivered mass). The device was then disassembled and the radioactivity of each part, i.e., nozzle and mouth piece (SNU), syringe, syringe holder, power pack together with the filter and filter holder was measured using the gamma camera to calculate the mass balance of the radiolabel (radioactivity distribution)[3].

The results listed in Table 1 show that the mass of the drug solution delivered from the device after 6 actuations is accurate and very close to the unlabelled formulation. This result indicates that radiolabelling of the 20% w/v Tobramycin solution using a spiking method did not alter the performance of the drug formulation/device. The radioactivity delivered from the syringe was between 16.7-20.6 MBq. However, these values are for information only and given the actual radioactivity delivered to the volunteer will be less than this value as this figure includes the radioactivity lost during the priming.

TABLE 1

Delivery of Tobramycin using Tobrair ® device

| Test 104418-01 | Mass delivered from the device (mg) | Radioactivity of the Tobramycin solution in the syringe (MBq) Before dosing | After dosing | Radioactivity delivered from the syringe (MBq) |
|---|---|---|---|---|
| a | 314.0 Mean | 26.9 | 6.3 | 20.6 Mean |
| b | 286.4  300.4 | 26.9 | 7.6 | 17.3  18.2 |
| c | 300.8  RSD 4.6% | 18.6* | 1.9 | 16.7 |

*Relatively low radioactivity due to slightly low initial formulation loading

The radioactivity distribution of the radiolabelled 20% w/v Tobramycin solution after delivery from Tobrair® device is shown in Table 2. A relatively high variability between the 3 tests was observed, which was thought to be due to the variable initial formulation loading into the syringe as such loading could not be accurately controlled. Since the delivered drug (and radiolabel) dose is controlled by the device, the accuracy of drug loading (and hence the total radioactivity) is not critical (as long as this is enough for 6 actuations). However, the variability in the initial drug loading can lead to different residual levels of formulation left in the syringe after dosing, which obviously will affect the result of the total mass balance. Therefore, the mass balance with the exclusion of the syringe would be more accurate to reflect the distribution of delivered dose and the formulation left in the SNU, device, etc. Such distribution is shown in Table 3 and FIG. 1, which indicates that relatively high dose delivery efficiency (54-72%), can be achieved using the Tobrair® device. Based on the percentage of the drug delivered and radioactivity delivered from the syringe (measured using CapinTec, Model no: CRC-15R) after 6 actuations, the delivered radioactivity from Tobrair® device is between 2.4-4.1 MBq when the drug solution has a radioactivity level of 42.8 MBq/mL at the targeted time (Table 3). At these levels of radioactivity, it was thought to be sufficient for in vitro gamma camera imaging. However if a higher level of radioactivity is required for better scintigraphic images, the initial radioactivity level can be adjusted accordingly.

TABLE 2

Delivery of 20% w/v Tobramycin solution using Tobrair ® device (mass balance)

| | Test 104418-1 | | | | | |
|---|---|---|---|---|---|---|
| | 1a | | 1b | | 1c | |
| SNU ID | 4460C0142 | | 4460C0144 | | 4460C0232 | |
| | Cps | % | Cps | % | Cps | % |
| Syringe | 450 | 30.3 | 471 | 34.8 | 107 | 11.2 |
| Syringe holder | 178 | 12.0 | 65 | 4.8 | 68 | 7.1 |
| SNU | 299 | 20.1 | 219 | 16.2 | 166 | 17.4 |
| Powerpack | 0 | 0.0 | 3 | 0.2 | 3 | 0.4 |
| Inhalation filter | 510 | 34.3 | 575 | 42.4 | 470 | 49.3 |
| Adaptor | 50 | 3.4 | 22 | 1.6 | 139 | 14.6 |
| Total | 1487 | 100.0 | 1355 | 100.0 | 953 | 100.0 |

TABLE 3

Delivery of 20% w/v Tobramycin using Tobrair ® device after 6 actuations

| | Test 104418-1 | | | | | |
|---|---|---|---|---|---|---|
| | 1a | | 1b | | 1c | |
| SNU ID | 4460C0142 | | 4460C0144 | | 4460C0232 | |
| | Cps | % | Cps | % | Cps | % |
| Syringe holder | 178 | 17.2 | 65 | 7.4 | 68 | 8.0 |
| SNU | 299 | 28.8 | 219 | 24.8 | 166 | 19.6 |
| Powerpack | 0 | 0.0 | 3 | 0.3 | 3 | 0.4 |
| Delivered dose* | 560 | 54.0 | 597 | 67.5 | 609 | 72.0 |
| Total | 1903 | 100.0 | 884 | 100.0 | 846 | 100.0 |
| Delivered radioactivity**# | 4.13 MBq | | 2.42 MBq | | 2.61 MBq | |

*sum of inhalation filter & adaptor
**based on the mass balance (measured using gamma camera) and radioactivity in the syringe (measured using both gamma camera and CapinTec).
these tests were conducted approximately 5 hours post targeted time (08:00 am). The low level of radioactivity was due to the decay of $^{99m}$Tc which has a half-life of 6 hours.

Radiolabelling of the 18% w/v Tobramycin Solution

A revised formulation/device combination was selected for use in the clinical study. This required the delivery of an 18% w/v solution×0.35 mL over 7 inhalations. Therefore, the in vitro delivery of $^{99m}$Tc-DTPA radiolabelled Tobramycin solution via Tobrair® device was repeated using the 18% w/v Tobramycin solution. The radiolabelling method was mostly the same as previously described. Briefly, the $^{99m}$Tc solution was eluted and $^{99m}$Tc-DTPA solution was prepared using a DTPA kit. The calculated volume of $^{99m}$Tc-DTPA solution (approximately 0.15 mL containing 482 MBq radioactivity) was added into a vial containing 10 mL pre-filtered 18% w/v Tobramycin solution provided by Xellia and thoroughly mixed with magnetic stirring. The radioactivity level in the resulting Tobramycin solution was 48.2 MBq/mL giving 16.9 MBq radioactivity per 0.35 mL dose. No change in colour of the radiolabelled 18% w/v Tobramycin solution or drug precipitation was observed after radiolabelling indicating compatibility of the radiolabel with the drug product.

In Vitro Delivery of the 18% w/v Tobramycin Using Tobrair® Device

Prior to the test approximately 0.7 mL of radiolabelled 18% w/v Tobramycin solution was loaded into the drug cartridge. After priming, the SNU was rinsed with water to remove the residual formulation and the remaining water was removed by gentle tapping on a piece of paper towel. The test conditions for dosing delivery were the same as described above for the 20% w/v Tobramycin solution. The delivered mass after 7 actuations was determined and the mass balance of the radiolabelled solution (i.e. radioactivity distribution) was also calculated.

It was noticed that the mass of the drug solution delivered from the device after 7 actuations was approximately 0.45 mL which was 28% higher than expected 0.35 mL (Table 4). Without being held to theory, this relatively high delivery mass was thought to be due to the contribution from the residual saline (used in device assembly) and water (used for rinsing) which remained in the SNU. In this experiment, in order to replicate the same procedure planned for the clinical study; the mouth piece was rinsed with water and tapped to dry rather than previously wiped with tissue before actuation. With this procedure it is possible that a small amount of water still remained in the SNU and would be evaporated during inhalation causing the apparent higher weight loss.

TABLE 4

Delivery of 18% w/v Tobramycin using Tobrair ® device

| Test Number | Mass delivered from the device (mg) | (mL)* | | Radioactivity of the drug solution in the syringe (MBq) | | Radioactivity delivered from the syringe (MBq) |
|---|---|---|---|---|---|---|
| | | | | Before dosing | After dosing | |
| 3a | 457.1 | 0.410 | Mean 0.449 RSD 8.2% | 36.6 | 10.43 | 26.17 (primed once) |
| 3b | 539.0 | 0.483 | | 39.9 | 3.88 | 36.02 (primed 3 times)** |
| 3c | 505.3 | 0.453 | | 41.8 | 10.51 | 31.29 (primed once) |

*based on density of 1.115 g/mL
**Device was primed 3 times due to short actuation time observed.

Figure 2:
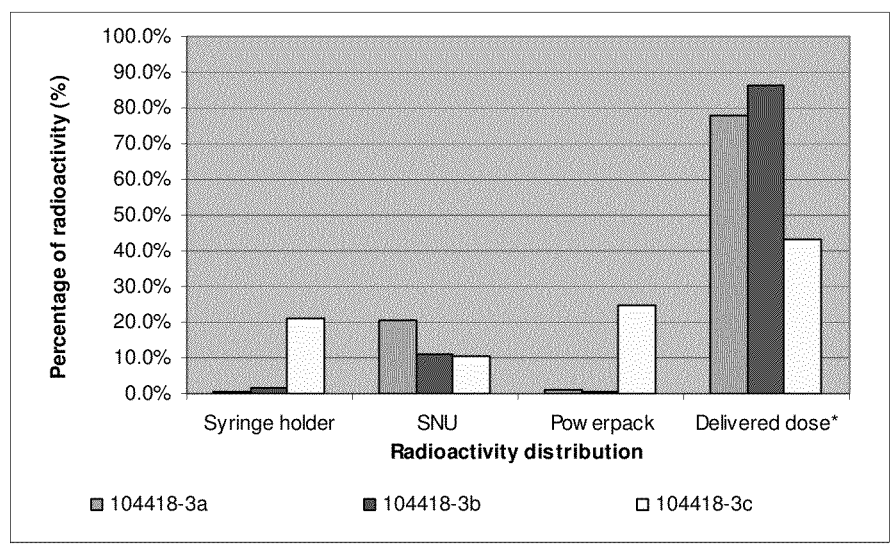
FIG. 2 shows the mass balance of radiolabelled Tobramycin solution delivered in vitro using a Tobrair® device.
Figure 3:
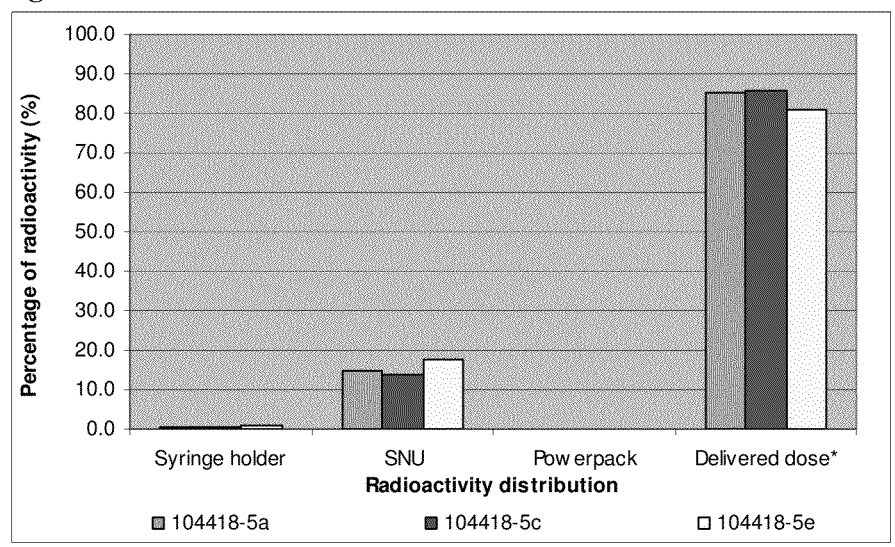
FIG. 3 shows the mass balance of radiolabelled 18% w/v Tobramycin solution delivered in vitro via a Tobrair® device.

The radioactivity delivered from the syringe is between 26.17-36.02 MBq. However, as previously discussed, these values include the delivered radioactivity during the priming and hence do not represent the actual radioactivity delivered to the volunteer. After delivery of the radiolabelled 18% w/Tobramycin solution by the Tobrair® device, the distribution of radioactivity in each part was measured using the gamma camera. As the variability in the initial drug loading into the syringe can affect the result of the mass balance, the mass balance with the exclusion of the syringe was calculated and shown in Table 5 and FIG. 2. Results from tests 3a and 3b indicate that the relatively high dose delivery efficiency (77.8 and 86.1%) can be achieved using the Tobrair® device. However, relatively low radioactivity was delivered from test 3c and, in contrast, unexpected relatively high radioactivity in syringe holder and powerpack was observed. The initial thought for this issue was due to the formulation leakage during the actuation. However, such leakage would lead to lower mass delivery (weight loss) as the leaked formulation would still remain in the device rather than be delivered to the inhalation filter but in fact total mass delivered from test 3c is no difference from the other two tests (Table 4). Therefore, the formulation leakage during the device actuation was ruled out. Another possibility is the sample cross-contamination during the device dissembling or radioactivity measurement. This has been confirmed by the delivered radioactivity result of experiment 3c in Table 5 which showed a relatively low radioactivity despite the delivered dose mass of experiment 3c was similar to 3a and 3b. Nevertheless, the results from all 3 tests show that at this radioactivity level i.e. 48.2 MBq/mL the delivered radioactivity is within the required range.

TABLE 5

Delivery of 18% w/v Tobramycin solution using Tobrair ® device (mass balance)

| | Test 104418-03 | | | | | |
|---|---|---|---|---|---|---|
| | 3a | | 3b | | 3c | |
| SNU ID | 4520C1251 | | 4520C1250 | | 4520C1242 | |
| | Cps | % | Cps | % | Cps | % |
| Syringe holder | 5.9 | 0.4 | 25.1 | 1.8 | 350.0 | 21.2 |
| SNU | 335.4 | 20.7 | 161.5 | 11.4 | 174.9 | 10.6 |

TABLE 5-continued

Delivery of 18% w/v Tobramycin solution using Tobrair ® device (mass balance)

| | | | | | | |
|---|---|---|---|---|---|---|
| Powerpack | 19.3 | 1.2 | 9.9 | 0.7 | 411.9 | 24.9 |
| Delivered dose* | 1260.0 | 77.7 | 1231.7 | 86.1 | 717.1 | 43.5 |
| Total | 1620.0 | 100.0 | 1428.3 | 100.0 | 1654.0 | 100.0 |
| Delivered radioactivity**# | 9.96 MBq | | 10.88 MBq | | 6.42 MBq | |

*sum of inhalation filter & adaptor
**based on the mass balance (measured using gamma camera) and radioactivity in the syringe (measured using both gamma camera and CapinTec).
these tests were conducted approximately 3.5 hours post targeted time (10:30 am). The low level of radioactivity was due to the decay of $^{99m}$Tc which has a half-life of 6 hours.

In addition, a short actuation time was observed in the experiments 3b and 3c. The time from actuation to the stop click was less than 3.5 seconds which was the recommended actuation time. The stop click occurred almost immediately after the actuation. A loose fitting between the syringe tip and SNU cavity or damage on the SNU's silicon chip would probably affect the actuation time which could be 1.5 second or less. This issue will be further discussed below.

Mass Weight Loss of the 18% w/v Tobramycin After Delivered Using Tobrair® Device During the in vitro test on delivery of the 18% w/v Tobramycin using the Tobrair® device it was noticed that the mass of the drug solution delivered from the device after 7 actuations was 28% higher than the expected 0.35 mL. This relatively high mass delivery was thought to be due to the co-evaporation of water and saline which were used for rinsing the drug formulation after the priming and removal of trapped air in the SNU Luer cavity. In order to confirm this hypothesis, a mass weight loss test was conducted using the decayed radiolabelled 18% w/v Tobramycin solution used in the previous experiment. The device was primed and dried using the same method as described above. The device was then connected to the Copley flow pump which was operated at 45 L/min for 140 seconds (similar to the total time required for 7 actuations) but without actual actuation of the device. The weight of the device was measured before and after this process to calculate the evaporation of the residual water evaporation. The device was then actuated for 7 times as normal procedure and further weight loss was measured.

TABLE 6

| Mass weight loss from Tobrair ® device | | | | | | | |
|---|---|---|---|---|---|---|---|
| | | Weight of device* (g) | | | Weight loss (g) | | |
| Test 104418-04 | SNU ID No. | Initial weight | After 140 sec with pump on | After 7 actuations | After 140 sec with pump on | after 7 actuations | Formulation delivered (mL)** |
| 4a | 4520C1356 | 151.3630 | 151.2634 | 150.8831 | 0.0996 | 0.3803 | 0.34 |
| 4b | 4520C1244 | 151.3278 | 151.2593 | 150.8902 | 0.0685 | 0.3691 | 0.33 |
| 4c | 4520C1453 | 150.9125 | 150.9046 | 150.5377 | 0.0079 | 0.3669 | 0.33 |
| | | Mean (RSD) | | | | 0.3721 (1.9%) | 0.33 (1.9%) |

*include syringe

**based on density 1.115 g/mL

The results listed in Table 6 indicated that water residue in the SNU did affect the total weight loss and after evaporating the residual water by running the air flow pump at 45 L/min for 140 seconds, the real weight loss from the delivered formulation is 0.37 g. Considering the formulation density of 1.115 g/mL the mean delivered volume should be 0.334 mL which is only 4.6% below the required dose. This experiment confirms that with 7 actuations Tobrair 4 device can actually deliver an accurate dose of 18% w/v Tobramycin solution for the clinical study.

The actuation time was observed throughout the 3 delivery experiments 104418-04a, 4b and 4c. It was noticed that each of the 7 actuations in experiment 4b and 4c were approximately 3.5 seconds. However in experiment 4a, there were 2 actuations (actuation 6 and 7) that had shorter actuation times of approximately 1 second.

In Vitro Delivery of Radiolabelled 18% w/v Tobramycin Using Tobrair® Device

The in vitro delivery of radiolabelled 18% w/v Tobramycin solution via the Tobrair® device was repeated to confirm that the dose delivered is appropriate and also to demonstrate that each of the 7 actuations was aerosolized in approximately 3.5 seconds.

A 10 mL pre-filtered 18% w/v Tobramycin solution was radiolabelled with 0.15 mL (1.5% of the total volume of drug solution) of $^{99m}$Tc-DTPA kit. The radioactivity of the 18% w/v Tobramycin solution was 46.4 MBq/mL giving 16.24 MBq per 0.35 mL at targeted time. This solution was filled into 5 syringes (nominal fill volume is 0.7 mL) for testing. Syringes 5b and 5d were assembled but not tested due to short actuation time observed during priming. The delivered dose and mass balance tests were conducted with a 140 second lag time introduced prior to device actuation to remove any residual saline and water in the SNU. The results in Table 7 demonstrated the delivered dose is within the 10% range of the nominal dose i.e. 0.35 mL of 18% w/v Tobramycin solution in 7 actuations. The results listed in Table 8 confirmed that the radioactivity delivered was within the range of 10 to 20 MBq. The mass balance of the radiolabelled solution (Table 8 and FIG. 4) demonstrated that high dose delivery efficiency (68% to 84%) can be achieved using the Tobrair® device.

Based on the timer on the Copley flow controller, model no: TPK, all 7 actuations time from these 3 experiments were not less than 3 seconds. No contamination or leakage was detected from the gamma camera images (FIG. 3).

TABLE 7

| Mass weight loss from Tobrair ® device | | | | | | | |
|---|---|---|---|---|---|---|---|
| | | Weight of device* (g) | | | Weight loss (g) | | |
| Test 104418-05 | SNU ID No. | Initial weight | After 140 sec with pump on | After 7 actuations | After 140 sec with pump on | after 7 actuations | Formulation delivered (mL)** |
| 5a | W4460C1032 | 151.1825 | 151.1014 | 150.7049 | 0.0811 | 0.3965 | 0.36 |
| 5c | 4520C1237 | 151.0915 | 151.0041 | 150.5983 | 0.0874 | 0.4058 | 0.36 |
| 5e | 4520C1450 | 151.2655 | 151.2193 | 150.857 | 0.0462 | 0.3623 | 0.32 |
| | | Mean (RSD) | | | | 0.3882 (5.9%) | 0.35 (5.9%) |

TABLE 8

Mass balance of Radiolabelled 18% w/v Tobramycin solution delivered using Tobrair ® device

| | Test 104418-05 | | | | | |
|---|---|---|---|---|---|---|
| | 5a | | 5c | | 5e | |
| SNU ID | W4460C1032 | | 4520C1237 | | 4520C1450 | |
| Mass balance after 7 actuations | Cps | % | Cps | % | Cps | % |
| Syringe holder | 7.1 | 0.2% | 9.5 | 0.5% | 24.4 | 1.2% |
| SNU | 425.0 | 14.6% | 282.4 | 13.6% | 371.4 | 17.8% |
| Powerpack | 3.5 | 0.1% | 2.8 | 0.1% | 3.6 | 0.2% |
| Inhalation Filter | 2446.6 | 84.0% | 1581.3 | 76.1% | 1414.6 | 67.8% |
| Adaptor | 30.8 | 1.1% | 203.0 | 9.8% | 272.9 | 13.1% |
| Total | 2913.1 | 100% | 2079.1 | 100% | 2086.8 | 100% |

TABLE 9

Delivery of Radiolabelled 18% w/v Tobramycin using Tobrair ® device after 7 actuations

| | Test 104418-05 | | | | | |
|---|---|---|---|---|---|---|
| | 5a | | 5c | | 5e | |
| SNU ID | W4460C1032 | | 4520C1237 | | 4520C1450 | |
| | Cps | % | Cps | % | Cps | % |
| Syringe holder | 7.1 | 0.2 | 9.2 | 0.5 | 24.4 | 1.2 |
| SNU | 425.0 | 14.6 | 275.4 | 13.3 | 371.4 | 17.8 |
| Powerpack | 3.5 | 0.1 | 2.8 | 0.1 | 3.6 | 0.2 |
| Delivered dose* | 2477.4 | 85.0 | 1784.4 | 86.1 | 1687.5 | 80.9 |
| Total | 2913.1 | 100.0 | 2071.8 | 100.0 | 2086.8 | 100.0 |
| Delivered radioactivity** | 21.75 MBq[#] | | 18.74 MBq | | 16.42 MBq | |

*sum of filter & adaptor
**based on the mass balance (measured using gamma camera) and radioactivity delivered from the syringe (measured using CapinTec). The value is for information only.
[#]Experiment 5a was conducted 2 hours earlier than the targeted time (14:00 pm) which gave a slightly higher radioactivity at testing time.

The device was primed according to the latest version of "Instructions for Use of Tobrair test device". During device priming, although the syringe was securely fitted to the SNU cavity, it was found that the issue with inappropriate actuation time, i.e., 1 second or less, was not eliminated and was found to be dependent on the SNU and/or syringe used for the device assembly. After discussion with Medspray, it was thought that the first priming should be performed using the spanner to hold the dose setting knob followed by actuation. This is to ensure that the first dose does not release under high pressure that might damage the silicon chip inside the SNU. Furthermore, a syringe push in tool with controlled force has been provided and the tool should be used to attach the syringe into the SNU cavity.

In Vitro Delivery of Tobramycin (TOBI®) Using PARI LC® PLUS Jet Nebulizer

Radiolabelling of the TOBI® Solution

For the comparison with prior art Tobramycin solution and the prevailing delivery system used, a TOBI® solution (300 mg/5 mL Tobramycin) to be delivered using PART LC® PLUS jet nebulizer, an individual TOBI® unit was radiolabelled. The $^{99m}$Tc solution was eluted and $^{99m}$Tc-DTPA solution was prepared using a DTPA kit. The radioactivity of resulting $^{99m}$Tc-DTPA solution was measured and the vial was sealed and stored in a lead pot before use. The whole content of an ampoule of TOBI® solution (~5 mL) was transferred into a clean scintillation vial and the calculated volume of the $^{99m}$Tc-DTPA solution (approximately 0.07 mL containing 18.1 MBq/5 mL) was added to the drug solution and thoroughly mixed with magnetic stirring. No change in colour of the Tobramycin solution or drug precipitation was observed after the radiolabelling indicating compatibility of the radiolabel with TOBI® solution. The mean radioactivity level of the resulting drug solution was 18.1 MBq/unit dose and the total volume of the $^{99m}$Tc-DTPA solution in the final drug solution was approximately 1.4% 4, which will not have any significant impact on the properties of the final drug solution and hence will not affect device performance.

Delivery of TOBI® Tobramycin Using PARI LC® PLUS Jet Nebulizer

In vitro Tobramycin delivery via the PART LC® PLUS jet nebulizer was characterised using a Copley BRS1000 breath simulator with the standard tidal breathing mode (n=3):

Tidal volume: 500 mL
Frequency: 15 breaths-per-minute (bpm)
Inhalation/exhalation ratio: 1:1

Prior to the test the radiolabelled TOBI® solution was transferred from the scintillation vial into the drug chamber in the PARI LC® PLUS jet nebulizer. The weight of the radiolabelled TOBI® solution was measured and the radioactivity was then calculated (Table 10). The nebulizer was then assembled with an exhalation filter (PARI Filter/Valve set[9]) before connecting the device to the Copley BRS1000 breath simulator via an inhalation filter (for dose collection). The device was then operated using a PARI TurboBOY N compressor until dryness. After dosing, the weight of the device was measured again to calculate the delivered mass. The device was also disassembled and the radioactivity of each part, i.e., inhalation filter, exhalation filter, T-piece and PARI nebulizer was measured using the gamma camera to calculate the mass balance of the radiolabel (Table 11) cf. Laboratory write up: 104418-02 Delivered dose and Mass balance tests of radiolabelled TOBI solution via PARI LC PLUS Jet nebulizer, dated 2 Feb. 2010).

The results listed in Table 10 shows that mass of the radiolabelled TOBI® solution loaded in the device was slightly more than 5 g and the radioactivity in the device before dosing was between 15.5-19.5 MBq. However, after nebulising to dryness i.e. when an aerosol was no longer generated, there was still approximately 40% of original loaded mass left in the device (Table 10).

TABLE 10

Delivery of TOBI ® Tobramycin using
PARI LC ® PLUS nebulizer

| Test 104418-2 | Weight of TOBI ® Tobramycin solution in PARI device (g) | Radioactivity of TOBI Tobramycin solution loaded in the device* (MBq) @ 10:00 | Mass delivered (g) | Percentage of mass left in the device (%) |
|---|---|---|---|---|
| a | 5.2429 | 17.7 | NT** | — |
| b | 5.2424 | 15.5 | 3.0568 | 41.7 |
| c | 5.2457 | 19.5 | 3.3670 | 35.8 |

*calculated based on the weight of the solution
**not tested in error

TABLE 11

Delivery of TOBI ® Tobramycin using PARI
LC ® nebulizer (mass balance)

| | Test 104418-2 | | | | | |
|---|---|---|---|---|---|---|
| | a | | b | | c | |
| | Cps | | Cps | | Cps | |
| TOBI solution in PARI (before dosing) | 2083 | — | 1734 | — | 1748 | — |
| Nebulising until dryness | Distribution | | | | | |
| | Cps | % | Cps | % | Cps | % |
| Inhalation filter | 524.5 | 26.7 | 565.2 | 35.0 | 549.2 | 33.7 |
| Exhalation filter | 273.6 | 13.9 | 298.3 | 18.5 | 285.5 | 17.5 |
| PARI nebulizer | 1126.9 | 57.5 | 724.6 | 44.9 | 772.1 | 47.4 |
| T-piece | 36.4 | 1.9 | 25.7 | 1.6 | 22.1 | 1.4 |
| Total (after dosing) | 1961.4 | 100.0 | 1613.9 | 100.0 | 1628.9 | 100.0 |

Figure 4:
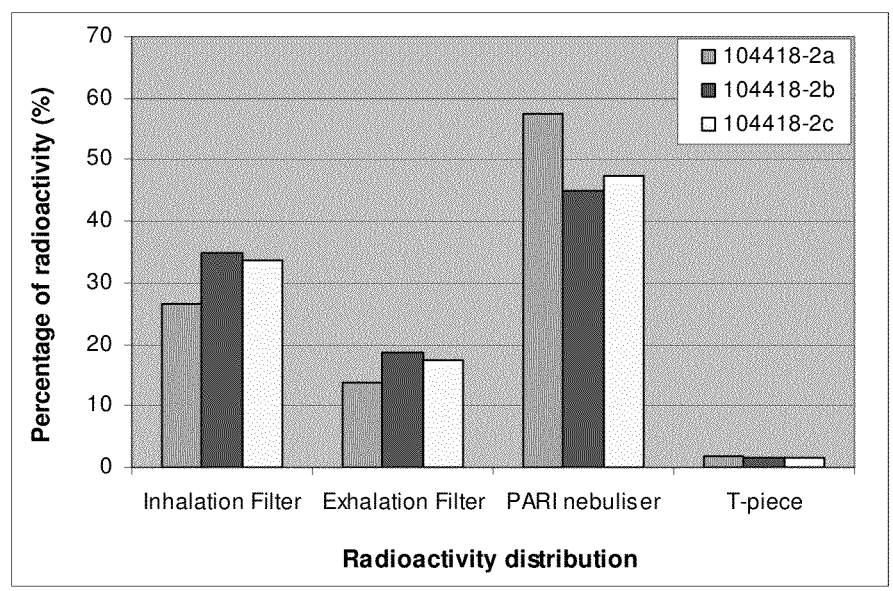
FIG. 4 shows the mass balance of radiolabelled TOBI® Tobramycin solution delivered in vitro using a PARI LC® Plus nebulizer.
Figure 5:
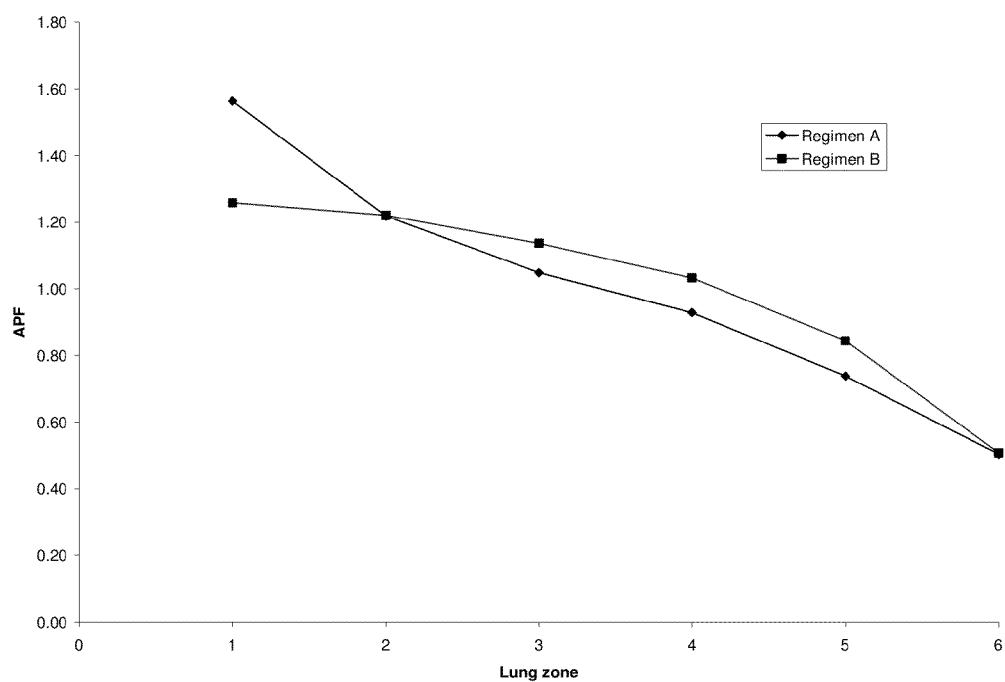
FIG. 5 shows the lung penetration profiles for all subjects being administered treatment regime A (60 mg Tobramycin delivered using the Tobrair® device) and treatment regime B (300 mg Tobramycin (TOBI®) delivered using the PARI LC® PLUS device system).

The mass balance of the radiolabelled TOBI® Tobramycin solution (represented as radioactivity) after delivery by PART LC® PLUS jet nebulizer is shown in Table 11 and FIG. 4. Based on the results it is expected that the percentage of the formulation deposited in the lungs (defined as the fraction in the inhalation filter) would be around 30%. The total delivered dose (sum of inhalation and exhalation filters) would be between 40.6-53.5% of the loaded dose (1 TOBI® unit=300 mg Tobramycin).

It is noted that the percentage of the radioactivity left in the device (approximately 50%) is higher than that of the mass (35.8-41.7%). Similar findings were reported by Gatnash et. al (Gatnash, A. A. et. al. (1998), "*A new method for measuring aerosol nebulizer output using radioactive tracers*", Eur. Respir. J., 12, pp. 467-471 on dose delivery from a nebulizer which was thought to be due to the water evaporation from the radiolabel (and the drug) solution during the mobilization. Because the drug concentration will not be constant during the nebulization it is not appropriate to determine the drug dose delivered by measuring the weight loss after the nebulisation. However, as both the drug and radiolabel are dissolved in the formulation and the change of radioactivity during the nebulisation would be corresponding to that of drug concentration; the delivered radioactivity would still be a good surrogate for delivered drug dose.

The in vitro characterisation results indicate that the $^{99m}$Tc-DTPA spiking method is suitable for radiolabelling of TOBI® Tobramycin solution for the clinical study although the percentage of dose (radioactivity) delivered via PARI LC® Plus nebulizer may be lower than that observed for the Tobrair® device. As a result, the radioactivity in the formulation should be targeted to be as high as possible, within the maximum allowable limit. This plus, the opportunity to increase of the image acquisition time during the clinical study will ensure that good quality images, suitable to achieve the study objectives, will be obtained.

Conclusion

Both Tobramycin solutions, i.e., concentrated 18% w/v solution and TOBI® 6% w/v solution were successfully radiolabelled with $^{99m}$Tc-DTPA using the spiking method. All radiolabelled drug solutions were clear and colourless with no precipitation present, hence there was no drug-radiolabel interaction observed. Good dose (radioactivity) delivery and mass balance results were found from the Tobrair® device which showed relatively higher efficiency in terms of formulation delivery than that from PARI LC® Plus nebulizer. It is concluded that $^{99m}$Tc-DTPA is a good surrogate marker for use in the gamma scintigraphic study and the level of radioactivity to be used for 18% w/v Tobramycin solution and TOBI® 6% w/v Tobramycin solution is not more than (NMT) 20 MBq per 0.35 mL and NMT 20 MBq per 1 TOBI® unit (~5 mL), respectively, which will be suitable for dosing to the volunteers.

Example 2

In Vivo Data; Comparison Between Prior Art Administration Regime and the Treatment Regime According to the Present Invention To assess the lung deposition of Tobramycin according to the therapeutic method according to the present disclosure, a two way non-randomised crossover study to studying the pulmonary distribution and pharmacokinetics in healthy subjects following single dose administration of Tobramycin via the Tobrair® device and PARI LC® PLUS jet nebulizer was performed. The study was designed as an open-labelled study as it is not possible to mask the identity of the aerosol delivery system used.

18 healthy, voluntary males and healthy, voluntary, non-pregnant, non-lactating females where subjected to the following treatment regimes:
  Approximately 63 mg Tobramycin (180 mg/mL×0.35 mL) delivered to the lungs via the novel Tobrair® device over 7 deep, slow inhalations.
  300 mg Tobramycin (TOBI®, 60 mg/mL×5 mL) delivered to the lungs via the PARI LC® PLUS jet nebulizer using relaxed tidal breathing to dryness or max 30 minutes.

The method used to measure lung deposition of Tobramycin is the well-established radionuclide imaging technique of gamma scintigraphy (Prescribing Information, TOPI® Tobramycin solution for Inhalation (Package Insert), Seattle, Wash.: Chiron Corporation; 2004, Klastersku et al., *Comparative studies of intermittent and continuous administration of aminoglycosides in the treatment of bronchopulmonary infections due to gram-negative bacteria*", Rev. Infect Dis., 1981, 3(1), pp 74-83) which allows quantitative assessment of in vivo deposition from a pulmonary delivery system to be quantified. Gamma scintigraphy may also provide an assessment of the regional distribution of deposited drug or formulation in the lungs, with central regions representing mainly large airways and peripheral regions representing mainly small airways and alveoli.

The present clinical study was designed to compare the aerosol delivery characteristics (measured by in vivo lung deposition and administration time) of Tobramycin administered by inhalation to healthy subjects using the Tobrair® device with those using the PARI LC® PLUS jet nebulizer. Additionally, serum Tobramycin concentrations and pharmacokinetic parameters were determined to evaluate the correlation with Tobramycin lung deposition.

In order to use gamma scintigraphy to assess the bronchopulmonary distribution of Tobramycin, the drug solution was labelled with a gamma emitting radioisotope as a surrogate marker. More specifically, technetium-99m diethylene triamine pentacetic acid ($^{99m}$Tc-DTPA) was used in this study to achieve 10-20 MBq per dose using the Tobrair® device and PARI LC® PLUS jet nebulizer.

Safety was assessed as well by reviewing adverse events data and vital signs data including pulse oximetry and spirometry data.

The gamma scintigraphic measurements performed on the voluntary subjects shows that the administration of approx. 63 mg Tobramycin (i.e. 0.35 ml of a 180 mg/ml solution of Tobramycin) using an inhaler such as Tobrair® device provides similar lung penetration profile as the commercial available and prevailing administration regime, cf. FIG. 1. This result is surprising taking into account that the total amount available for administration in the Tobrair® device is considerably lower according to the method of the invention compared with the prevailing administration regime.

In addition, the results show that the less Tobramycin is exhaled when using regimen A compared with regimen B, cf. table 12 and below.

TABLE 12

Deposition pattern as percentage delivered dose for Regimen A - (approx. 63 mg Tobramycin delivered to the lungs via the Tobrair ® device)

| Subject Number | Whole lung (%) | Oropharyngeal 4 (%) | Exhaled air (%) | Tissues (%) |
|---|---|---|---|---|
| 0001 | 30.0 | 69.0 | 0.9 | 0.0 |
| 0002 | 27.9 | 71.9 | 0.1 | 0.0 |
| 0003 | 28.5 | 71.4 | 0.1 | 0.0 |
| 0004 | 11.9 | 85.1 | 0.2 | 2.9 |
| 00051 | 4.7 | 66.5 | 14.7 | 14.1 |
| 0006 | 19.9 | 79.6 | 0.4 | 0.1 |
| 0007 | 22.0 | 71.3 | 0.4 | 6.4 |
| 0008 | 15.4 | 81.9 | 0.9 | 1.8 |
| 00092 | 11.6 | 87.5 | 0.9 | 0.0 |
| 0010 | 16.3 | 83.1 | 0.6 | 0.0 |
| 0011 | 21.6 | 74.1 | 1.2 | 3.0 |
| 00123 | 18.2 | 81.2 | 0.6 | 0.0 |
| 0013 | 11.3 | 88.6 | 0.1 | 0.0 |
| 0014 | 11.6 | 88.2 | 0.2 | 0.1 |
| 0015 | 14.5 | 84.2 | 1.2 | 0.1 |
| 0016 | 7.8 | 79.0 | 12.9 | 0.4 |
| 0017 | 22.9 | 76.8 | 0.3 | 0.0 |
| 0018 | 20.9 | 78.8 | 0.2 | 0.0 |
| Mean | 17.61 | 78.79 | 1.99 | 1.61 |
| SD | 7.201 | 6.841 | 4.322 | 3.550 |
| Median | 17.25 | 79.30 | 0.50 | 0.05 |
| CV % | 40.9 | 8.7 | 216.7 | 221.1 |
| Min | 4.7 | 66.5 | 0.1 | 0.0 |
| Max | 30.0 | 88.6 | 14.7 | 14.1 |
| n | 18 | 18 | 18 | 18 |

1. Subject 0005 coughed during each of the 7 actuations
2. Device did not actuate correctly on 1st actuation attempt. Replacement device used for remaining 6 actuations
3. No actuation recorded for the 1st actuation attempt.
4. The sum of oral cavity, oropharynx, oesophagus, stomach

TABLE 13

Deposition pattern as percentage total fill for Regimen B - (300 mg Tobramycin (TOBI ®) delivered to the lungs via the PARI LC ® PLUS)

| Subject Number | Whole lung (%) | Oropharyngeal [1] (%) | Exhaled air (%) | Tissues (%) | Device[2] (%) |
|---|---|---|---|---|---|
| 0001 | 13.9 | 5.2 | 22.2 | 0.0 | 58.6 |
| 0002 | 20.2 | 11.6 | 30.9 | 0.6 | 36.7 |
| 0003 | 11.6 | 3.9 | 31.8 | 0.0 | 52.7 |
| 0004 | 8.1 | 7.7 | 21.4 | 0.3 | 62.4 |
| 0005 | 8.0 | 13.8 | 24.4 | 1.4 | 52.4 |
| 0006 | 8.3 | 7.8 | 27.5 | 0.0 | 56.4 |
| 0007 | 7.9 | 12.8 | 23.9 | 0.0 | 55.5 |
| 0008 | 6.8 | 13.6 | 24.4 | 0.1 | 55.1 |
| 0009 | 7.7 | 6.9 | 22.0 | 0.0 | 63.3 |
| 0011 | 13.7 | 12.4 | 51.4 | 0.1 | 22.4 |
| 0012 | 8.7 | 5.7 | 23.1 | 0.0 | 62.5 |
| 0013 | 19.5 | 18.2 | 42.0 | 0.0 | 20.2 |
| 0014 | 8.2 | 10.7 | 24.1 | 0.1 | 56.9 |
| 0015 | 12.1 | 14.3 | 33.6 | 0.1 | 40.0 |
| 0016 | 6.2 | 12.7 | 26.2 | 0.1 | 54.8 |
| 0017 | 13.9 | 8.2 | 29.9 | 0.1 | 47.9 |
| 0018 | 10.3 | 10.6 | 29.5 | 0.0 | 49.6 |
| Mean | 10.89 | 10.36 | 28.72 | 0.17 | 49.85 |
| SD | 4.197 | 3.848 | 7.879 | 0.351 | 12.924 |
| Median | 8.70 | 10.70 | 26.20 | 0.10 | 54.80 |
| CV % | 38.5 | 37.2 | 27.4 | 206.0 | 25.9 |
| Min | 6.2 | 3.9 | 21.4 | 0.0 | 20.2 |
| Max | 20.2 | 18.2 | 51.4 | 1.4 | 63.3 |
| n | 17 | 17 | 17 | 17 | 17 |

[1] The sum of oral cavity, oropharynx, oesophagus, stomach
[2] The sum of device, t-piece and mouthpiece The results also shows that the treatment regime according to the present disclosure (regime A) provides for similar deposition patterns and lung penetration profile in six lung regions (zone 1-6) as the prevailing administration regime (regime B), cf. table 14 below.

TABLE 14

Lung deposition pattern in six lung regions for Regimen A - (Approx. 63 mg Tobramycin delivered via the Tobrair ® device)

| Subject Number | Zone 1 (%) | Zone 2 (%) | Zone 3 (%) | Zone 4 (%) | Zone 5 (%) | Zone 6 (%) |
|---|---|---|---|---|---|---|
| 0001 | 26.9 | 9.8 | 12.8 | 16.7 | 18.3 | 15.6 |
| 0002 | 29.7 | 10.6 | 13.8 | 15.8 | 15.9 | 14.2 |
| 0003 | 21.3 | 10.0 | 14.5 | 17.5 | 20.3 | 16.3 |
| 0004 | 26.1 | 9.2 | 11.0 | 15.0 | 17.2 | 21.5 |
| 0005 | 33.1 | 8.8 | 11.5 | 12.6 | 15.6 | 18.3 |
| 0006 | 38.2 | 9.5 | 12.1 | 13.3 | 13.4 | 13.5 |
| 0007 | 27.7 | 10.6 | 10.8 | 16.3 | 19.6 | 15.0 |
| 0008 | 35.0 | 8.9 | 11.0 | 14.7 | 16.7 | 13.6 |
| 0009 | 31.5 | 9.5 | 10.5 | 13.5 | 15.4 | 19.5 |
| 0010 | 28.7 | 11.4 | 11.7 | 14.3 | 17.0 | 16.9 |
| 0011 | 29.2 | 8.7 | 13.0 | 15.9 | 18.4 | 14.8 |
| 0012 | 27.7 | 8.4 | 13.1 | 15.0 | 16.7 | 19.1 |
| 0013 | 27.5 | 9.3 | 11.4 | 16.0 | 17.9 | 17.9 |
| 0014 | 30.8 | 10.1 | 12.7 | 15.3 | 17.3 | 13.9 |
| 0015 | 32.5 | 8.4 | 12.0 | 15.5 | 16.5 | 15.0 |
| 0016 | 26.8 | 9.3 | 10.3 | 15.2 | 18.5 | 19.9 |
| 0017 | 39.5 | 11.0 | 12.1 | 14.0 | 13.7 | 9.8 |
| 0018 | 32.9 | 9.5 | 12.9 | 15.0 | 16.6 | 13.0 |
| Mean | 30.28 | 9.61 | 12.07 | 15.09 | 16.94 | 15.99 |
| SD | 4.460 | 0.869 | 1.160 | 1.237 | 1.792 | 2.949 |
| Median | 29.45 | 9.50 | 12.05 | 15.10 | 16.85 | 15.30 |
| CV % | 14.7 | 9.0 | 9.6 | 8.2 | 10.6 | 18.4 |
| Min | 21.3 | 8.4 | 10.3 | 12.6 | 13.4 | 9.8 |
| Max | 39.5 | 11.4 | 14.5 | 17.5 | 20.3 | 21.5 |
| n | 18 | 18 | 18 | 18 | 18 | 18 |

TABLE 15

Lung deposition pattern in six lung regions for Regimen B - (300 mg Tobramycin (TOBI ®) delivered via the PARI LC ® PLUS)

| Subject Number | Zone 1 (%) | Zone 2 (%) | Zone 3 (%) | Zone 4 (%) | Zone 5 (%) | Zone 6 (%) |
|---|---|---|---|---|---|---|
| 0001 | 20.7 | 9.1 | 12.3 | 17.4 | 21.6 | 18.8 |
| 0002 | 24.6 | 10.7 | 13.7 | 16.5 | 18.8 | 15.7 |
| 0003 | 19.8 | 10.6 | 13.2 | 18.6 | 20.8 | 17.1 |
| 0004 | 22.5 | 8.8 | 12.5 | 17.1 | 18.8 | 20.3 |
| 0005 | 24.5 | 10.8 | 14.8 | 16.6 | 17.7 | 15.7 |
| 0006 | 26.4 | 10.0 | 12.2 | 16.1 | 19.7 | 15.6 |
| 0007 | 19.7 | 8.9 | 11.7 | 16.4 | 23.1 | 20.4 |
| 0008 | 24.2 | 11.0 | 12.4 | 16.2 | 20.4 | 15.8 |
| 0009 | 26.7 | 8.6 | 11.5 | 16.4 | 20.2 | 16.6 |
| 0011 | 23.7 | 10.7 | 12.6 | 17.3 | 19.8 | 15.8 |
| 0012 | 26.2 | 9.1 | 13.1 | 15.5 | 19.7 | 16.4 |
| 0013 | 20.9 | 9.1 | 13.0 | 18.0 | 21.3 | 17.7 |
| 0014 | 28.3 | 9.9 | 13.2 | 15.7 | 18.2 | 14.8 |
| 0015 | 23.2 | 9.7 | 14.0 | 17.9 | 20.9 | 14.3 |
| 0016 | 21.5 | 8.1 | 12.0 | 15.8 | 19.9 | 22.7 |
| 0017 | 32.0 | 9.8 | 13.0 | 17.7 | 16.7 | 10.7 |
| 0018 | 28.3 | 10.6 | 14.8 | 17.1 | 17.5 | 11.7 |
| Mean | 24.31 | 9.74 | 12.94 | 16.84 | 19.71 | 16.48 |
| SD | 3.389 | 0.899 | 0.963 | 0.890 | 1.637 | 2.986 |
| Median | 24.20 | 9.80 | 13.00 | 16.60 | 19.80 | 15.80 |
| CV % | 13.9 | 9.2 | 7.4 | 5.3 | 8.3 | 18.1 |
| Min | 19.7 | 8.1 | 11.5 | 15.5 | 16.7 | 10.7 |
| Max | 32.0 | 11.0 | 14.8 | 18.6 | 23.1 | 22.7 |
| n | 17 | 17 | 17 | 17 | 17 | 17 |

TABLE 16

Lung penetration profile for six lung regions for Regimen A - (approx. 63 mg Tobramycin delivered via the Tobrair ® device)

| Subject Number | Airway penetration factors | | | | | |
|---|---|---|---|---|---|---|
|  | Zone 1 | Zone 2 | Zone 3 | Zone 4 | Zone 5 | Zone 6 |
| 0001 | 1.37 | 1.20 | 1.12 | 1.00 | 0.81 | 0.50 |
| 0002 | 1.46 | 1.32 | 1.15 | 0.92 | 0.71 | 0.45 |
| 0003 | 1.08 | 1.27 | 1.22 | 1.07 | 0.85 | 0.52 |
| 0004 | 1.40 | 1.19 | 1.03 | 0.95 | 0.77 | 0.66 |
| 0005 | 1.77 | 1.18 | 1.02 | 0.80 | 0.68 | 0.56 |
| 0006 | 1.98 | 1.25 | 1.00 | 0.79 | 0.59 | 0.39 |
| 0007 | 1.41 | 1.29 | 1.01 | 1.00 | 0.81 | 0.48 |
| 0008 | 1.81 | 1.14 | 0.96 | 0.92 | 0.73 | 0.45 |
| 0009 | 1.67 | 1.23 | 0.95 | 0.87 | 0.68 | 0.59 |
| 0010 | 1.45 | 1.40 | 1.05 | 0.87 | 0.72 | 0.52 |
| 0011 | 1.49 | 1.13 | 1.09 | 1.00 | 0.78 | 0.50 |
| 0012 | 1.46 | 1.17 | 1.10 | 0.96 | 0.75 | 0.57 |
| 0013 | 1.46 | 1.16 | 1.01 | 0.97 | 0.81 | 0.59 |
| 0014 | 1.57 | 1.24 | 1.04 | 0.93 | 0.76 | 0.45 |
| 0015 | 1.67 | 1.11 | 1.07 | 0.94 | 0.74 | 0.48 |
| 0016 | 1.45 | 1.18 | 0.93 | 0.97 | 0.85 | 0.63 |
| 0017 | 1.94 | 1.31 | 1.03 | 0.84 | 0.56 | 0.32 |
| 0018 | 1.70 | 1.19 | 1.09 | 0.91 | 0.70 | 0.41 |
| Mean | 1.563 | 1.220 | 1.048 | 0.928 | 0.739 | 0.504 |
| SD | 0.2229 | 0.0757 | 0.0727 | 0.0733 | 0.0793 | 0.0870 |
| Median | 1.475 | 1.195 | 1.035 | 0.935 | 0.745 | 0.500 |
| CV % | 14.3 | 6.2 | 6.9 | 7.9 | 10.7 | 17.3 |
| Min | 1.08 | 1.11 | 0.93 | 0.79 | 0.56 | 0.32 |
| Max | 1.98 | 1.40 | 1.22 | 1.07 | 0.85 | 0.66 |
| n | 18 | 18 | 18 | 18 | 18 | 18 |

TABLE 17

Lung penetration profile for six lung regions for Regimen B - (300 mg Tobramycin (TOBI ®) delivered via the PARI LC ® PLUS)

| Subject Number | Airway penetration factors | | | | | |
|---|---|---|---|---|---|---|
|  | Zone 1 | Zone 2 | Zone 3 | Zone 4 | Zone 5 | Zone 6 |
| 0001 | 1.13 | 1.15 | 1.11 | 1.08 | 0.96 | 0.58 |
| 0002 | 1.22 | 1.35 | 1.19 | 1.02 | 0.78 | 0.45 |
| 0003 | 1.01 | 1.27 | 1.19 | 1.10 | 0.90 | 0.52 |
| 0004 | 1.18 | 1.19 | 1.12 | 1.04 | 0.85 | 0.62 |
| 0005 | 1.25 | 1.30 | 1.20 | 1.02 | 0.76 | 0.47 |
| 0006 | 1.37 | 1.19 | 1.12 | 1.03 | 0.81 | 0.48 |
| 0007 | 1.06 | 1.13 | 1.11 | 1.05 | 1.00 | 0.66 |
| 0008 | 1.30 | 1.25 | 1.09 | 0.99 | 0.88 | 0.49 |
| 0009 | 1.42 | 1.13 | 1.07 | 1.01 | 0.86 | 0.52 |
| 0011 | 1.22 | 1.25 | 1.14 | 1.06 | 0.84 | 0.48 |
| 0012 | 1.37 | 1.15 | 1.13 | 1.01 | 0.83 | 0.51 |
| 0013 | 1.09 | 1.19 | 1.13 | 1.13 | 0.89 | 0.56 |
| 0014 | 1.45 | 1.25 | 1.11 | 0.94 | 0.78 | 0.46 |
| 0015 | 1.19 | 1.20 | 1.19 | 1.08 | 0.87 | 0.47 |
| 0016 | 1.14 | 1.14 | 1.05 | 1.04 | 0.93 | 0.70 |
| 0017 | 1.57 | 1.32 | 1.14 | 0.95 | 0.70 | 0.33 |
| 0018 | 1.40 | 1.32 | 1.23 | 1.00 | 0.70 | 0.35 |
| Mean | 1.257 | 1.222 | 1.136 | 1.032 | 0.844 | 0.509 |
| SD | 0.1542 | 0.0724 | 0.0489 | 0.0496 | 0.0832 | 0.0961 |
| Median | 1.220 | 1.200 | 1.130 | 1.030 | 0.850 | 0.490 |
| CV % | 12.3 | 5.9 | 4.3 | 4.8 | 9.9 | 18.9 |
| Min | 1.01 | 1.13 | 1.05 | 0.94 | 0.70 | 0.33 |
| Max | 1.57 | 1.35 | 1.23 | 1.13 | 1.00 | 0.70 |
| n | 17 | 17 | 17 | 17 | 17 | 17 |

Furthermore, the treatment regime according to the present disclosure provides for a shorter administration time compared with the prevailing administration regime (regime B). The time used to inhale the Tobramycin dose according to treatment regime A, i.e. by 7 deep, slow inhalations took less than 60 sec to perform. This is illustrated by the results shown in table 18 wherein the time taken for each of the 7 inhalations is recorded.

TABLE 18

Actuation times (sec) for all subjects following the treatment regime according to the present invention (regimen A)

| Subject Number | Actuation | | | | | | | Mean | SD | Median | CV % | Min | Max | n |
|---|---|---|---|---|---|---|---|---|---|---|---|---|---|---|
|  | 1 | 2 | 3 | 4 | 5 | 6 | 7 |  |  |  |  |  |  |  |
| 0001 | 2.851 | 3.813 | 3.718 | 3.770 | 3.907 | 3.899 | 3.938 | 3.6994 | 0.38251 | 3.8130 | 10.3 | 2.851 | 3.938 | 7 |
| 0002 | 3.305 | 3.438 | 3.661 | 3.751 | 3.740 | 3.833 | 3.902 | 3.6614 | 0.21543 | 3.7400 | 5.9 | 3.305 | 3.902 | 7 |
| 0003 | 3.779 | 3.779 | 3.853 | 3.832 | 3.864 | 3.936 | 3.929 | 3.8531 | 0.06348 | 3.8530 | 1.6 | 3.779 | 3.936 | 7 |
| 0004 | 3.816 | 3.827 | 3.814 | 3.842 | 3.880 | 3.843 | 3.829 | 3.8359 | 0.02249 | 3.8290 | 0.6 | 3.814 | 3.880 | 7 |
| 0005 | 3.942 | 4.418 | 4.348 | 4.632 | 4.928 | 5.246 | 5.607 | 4.7316 | 0.56985 | 4.6320 | 12.0 | 3.942 | 5.607 | 7 |
| 0006 | 3.252 | 3.573 | 3.792 | 3.841 | 3.968 | 4.073 | 4.013 | 3.7874 | 0.28885 | 3.8410 | 7.6 | 3.252 | 4.073 | 7 |
| 0007 | 2.885 | 3.782 | 3.545 | 3.881 | 3.539 | 3.453 | 3.388 | 3.4961 | 0.32174 | 3.5390 | 9.2 | 2.885 | 3.881 | 7 |
| 0008 | 3.148 | 3.337 | 3.386 | 3.418 | 3.390 | 3.361 | 3.413 | 3.3504 | 0.09361 | 3.3860 | 2.8 | 3.148 | 3.418 | 7 |

TABLE 18-continued

Actuation times (sec) for all subjects following the treatment regime according to the present invention (regimen A )

| Subject | Actuation | | | | | | | | | | | | | |
|---|---|---|---|---|---|---|---|---|---|---|---|---|---|---|
| Number | 1 | 2 | 3 | 4 | 5 | 6 | 7 | Mean | SD | Median | CV % | Min | Max | n |
| 0009[1] | 0.043 | 2.868 | 3.099 | 3.139 | 3.024 | 3.190 | 3.167 | 2.6471 | 1.15350 | 3.0990 | 43.6 | 0.043 | 3.190 | 7 |
| 0010 | 3.329 | 3.537 | 3.541 | 3.591 | 3.582 | 3.571 | 3.607 | 3.5369 | 0.09511 | 3.5710 | 2.7 | 3.329 | 3.607 | 7 |
| 0011 | 3.759 | 3.726 | 3.734 | 3.747 | 3.814 | 3.752 | 3.792 | 3.7606 | 0.03163 | 3.7520 | 0.8 | 3.726 | 3.814 | 7 |
| 0012[2] | | 3.708 | 3.715 | 3.789 | 3.758 | 3.792 | 3.799 | 3.7602 | 0.04030 | 3.7735 | 1.1 | 3.708 | 3.799 | 6 |
| 0013 | 3.831 | 3.796 | 3.778 | 3.806 | 3.815 | 3.770 | 3.814 | 3.8014 | 0.02162 | 3.8060 | 0.6 | 3.770 | 3.831 | 7 |
| 0014 | 3.185 | 3.405 | 3.400 | 3.562 | 3.613 | 3.544 | 3.509 | 3.4597 | 0.14464 | 3.5090 | 4.2 | 3.185 | 3.613 | 7 |
| 0015 | 3.171 | 3.636 | 3.633 | 3.718 | 3.863 | 4.065 | 4.490 | 3.7966 | 0.40975 | 3.7180 | 10.8 | 3.171 | 4.490 | 7 |
| 0016 | 3.349 | 3.539 | 3.530 | 3.592 | 3.604 | 3.542 | 3.621 | 3.5396 | 0.09124 | 3.5420 | 2.6 | 3.349 | 3.621 | 7 |
| 0017 | 3.119 | 3.333 | 3.410 | 3.501 | 3.438 | 3.496 | 3.505 | 3.4003 | 0.13871 | 3.4380 | 4.1 | 3.119 | 3.505 | 7 |
| 0018 | 3.051 | 3.248 | 3.361 | 3.455 | 3.421 | 3.470 | 3.475 | 3.3544 | 0.15593 | 3.4210 | 4.6 | 3.051 | 3.475 | 7 |

[1]Device did not actuate correctly on 1st actuation attempt. Replacement device used for remaining 6 actuations.

[2]No actuation recorded for the 1st actuation attempt

TABLE 19

Plasma levels of treatment 1 (=Treatment regime A, Tobrair) compared to treatment 2 (Treatment regime B, TOBI).

| Subject | Treatment | time hours | plasma levels ng/mL | Dose mg | $AUC_{0-8\ ngxh/mL}$ | $AUC_{0-inf\ ngxh/mL}$ | $C_{max\ ng/mL}$ | $T_{max\ h}$ | $T_{1/2\ h}$ | Elim rate const | $F_{rel}$ |
|---|---|---|---|---|---|---|---|---|---|---|---|
| 1 | 1 | 0 | 0 | | | | | | | | |
| | | 0.5 | 211 | | 1857 | 2412 | 264 | 2 | 4.63 | 0.1495 | |
| | | 1 | 239 | | | | | | | | |
| | | 2 | 264 | | | | | | | | |
| | | 4 | 250 | | | | | | | | |
| | | 8 | 113 | | | | | | | | |
| 1 | 2 | 0 | 0 | | | | | | | | |
| | | 0.5 | 345 | | 4408 | 6372 | 700 | 4 | 3.93 | 0.1752 | |
| | | 1 | 569 | | | | | | | | |
| | | 2 | 678 | | | | | | | | |
| | | 4 | 700 | | | | | | | | |
| | | 8 | 346 | | | | | | | | |
| 1 to 18 | 1 | 0 | 0 | | | | | | | | |
| | | 0.5 | 100 | 12.34 | 914 | 1205 | 162 | 2 | 3.70 | 0.1874 | 0.28 |
| | | 1 | 148 | | | | | | | | |
| | | 2 | 162 | | | | | | | | |
| | | 4 | 134 | | | | | | | | |
| | | 8 | 54 | | | | | | | | |
| 1 to 18 | 2 | 0 | 0 | | | | | | | | |
| | | 0.6 | 262 | 32.31 | 3317 | 4491 | 590 | 2 | 3.88 | 0.1787 | |
| | | 1 | 517 | | | | | | | | |
| | | 2 | 590 | | | | | | | | |
| | | 4 | 498 | Relativ | 0.38 | | | | | | |
| | | 8 | 210 | dosis | | | | | | | |

The invention claimed is:

1. A method for preventing or treating bacterial infections in the pulmonary system of a patient in need thereof comprising administering by inhalation an aerosolized dose of an aqueous solution of 150-250 mg/ml of an aminoglycoside antibiotic, wherein administering is with a metered dose inhalation device that provides an aerosol having a mass median aerodynamic diameter of 4-7 micrometer, wherein the metered dose inhaler has a spray nozzle unit providing said aerosols by transferring the composition through orifices.

2. The method of claim 1, wherein the aminoglycoside antibiotic is Tobramycin.

3. The method of claim 2, wherein the Tobramycin is Tobramycin sulphate corresponding to 150-250 mg/ml of Tobramycin.

4. The method of claim 3, wherein the Tobramycin is Tobramycin sulphate corresponding to 180 mg/ml of Tobramycin.

5. The method of claim 3, wherein the aqueous solution of 150-250 mg/ml of Tobramycin sulphate is free of added sodium chloride.

6. The method of claim 5, wherein the aqueous solution of Tobramycin sulphate has a pH of 6-8.

7. The method of claim 3, wherein inhalation is performed in less than 5 minutes.

8. The method of claim 3, wherein administering is by breath actuated inhalation and the patient performs 7 inhalations.

9. The method of claim 3, wherein inhalation is performed in less than 4 minutes.

10. The method of claim 3, wherein inhalation is performed in less than 3 minutes.

11. The method of claim 3, wherein inhalation is performed in less than 2 minutes.

12. The method of claim 3, wherein inhalation is performed in less than 1 minute.

13. The method of claim 3, wherein the volume of the dose to be aerosolized is 500 microliters.

14. The method of claim 3, wherein the amount of Tobramycin sulfate to be administered is 50 to 80 mg/dose.

15. The method of claim 1, wherein the metered dose inhaler provides a working pressure of 20-80 bar.

16. The method of claim 3, wherein the Tobramycin sulphate is present at 180 mg/ml and the metered dose inhaler provides a working pressure of 30-40 bar.

17. The method of claim 1, wherein the metered dose inhaler provides a flow of 10-50 L/min.

18. The method of claim 1, wherein the patient is in need of treatment for cystic fibrosis.

* * * * *